(12) United States Patent
Schlom et al.

(10) Patent No.: US 10,550,164 B2
(45) Date of Patent: Feb. 4, 2020

(54) BRACHYURY DELETION MUTANTS, NON-YEAST VECTORS ENCODING BRACHYURY DELETION MUTANTS, AND THEIR USE

(71) Applicant: The United States of America, as represented by the Secretary, Department of Health and Human Services, Bethesda, MD (US)

(72) Inventors: Jeffrey Schlom, Potomac, MD (US); Claudia M. Palena, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 3 days.

(21) Appl. No.: 15/749,214

(22) PCT Filed: Aug. 3, 2016

(86) PCT No.: PCT/US2016/045289
§ 371 (c)(1),
(2) Date: Jan. 31, 2018

(87) PCT Pub. No.: WO2017/024000
PCT Pub. Date: Feb. 9, 2017

(65) Prior Publication Data
US 2018/0222951 A1    Aug. 9, 2018

Related U.S. Application Data

(60) Provisional application No. 62/200,438, filed on Aug. 3, 2015.

(51) Int. Cl.
| | |
|---|---|
| C07K 1/00 | (2006.01) |
| C07K 14/00 | (2006.01) |
| C07K 17/00 | (2006.01) |
| A61K 39/00 | (2006.01) |
| A61K 39/38 | (2006.01) |
| C07K 14/47 | (2006.01) |
| A61P 35/00 | (2006.01) |
| A61K 9/127 | (2006.01) |
| A61K 38/17 | (2006.01) |
| A61K 38/19 | (2006.01) |
| A61K 45/06 | (2006.01) |
| C12N 15/86 | (2006.01) |

(52) U.S. Cl.
CPC .......... *C07K 14/4702* (2013.01); *A61K 9/127* (2013.01); *A61K 38/1709* (2013.01); *A61K 38/193* (2013.01); *A61K 39/0011* (2013.01); *A61K 39/00117* (2018.08); *A61K 39/001152* (2018.08); *A61K 39/001182* (2018.08); *A61K 45/06* (2013.01); *A61P 35/00* (2018.01); *C12N 15/86* (2013.01); *A61K 2039/5256* (2013.01); *A61K 2039/70* (2013.01); *C12N 2710/10043* (2013.01); *Y02A 50/466* (2018.01)

(58) Field of Classification Search
CPC ......... A61K 38/00; A61K 39/00; C07K 14/47
See application file for complete search history.

(56) References Cited

FOREIGN PATENT DOCUMENTS

| | | |
|---|---|---|
| WO | WO 2008/106551 A2 | 9/2008 |
| WO | WO 2014/043518 A1 | 3/2014 |
| WO | WO 2014/043535 A1 | 3/2014 |

OTHER PUBLICATIONS

Amalfitano et al., "Production and Characterization of Improved Adenovirus Vectors with the E1, E2b, and E3 Genes Deleted," *J. Virol.*, 72(2): 926-933 (1998).
Gabitzsch et al., "Anti-tumor immunotherapy despite immunity to adenovirus using a novel adenoviral vector Ad5 [E1-, E2b-]-CEA," *Cancer Immunol. Immunother.*, 59(7): 1131-1135 (2010).
Gabitzsch et al., "The generation and analyses of a novel combination of recombinant adenovirus vaccines targeting three tumor antigens as an immunotherapeutic," *Oncotarget* 6(31): 31344-31359 (2015).
Genbank Accession No. NM_003181 (date Jun. 25, 2015).
Genbank Accession No. NP_003172 (date Jun. 25, 2015).
Jochems et al., "Identification and characterization of agonist epitopes of the MUC1-C oncoprotein," *Cancer Immunol. Immunother.*, 63(2): 161-174 (2014).
Lan et al., "Cloning and Sequencing of a Human Pancreatic Tumor Mucin cDNA," *J. Biol. Chem.*, 265(25): 15294-15299 (1990).
Li et al., "The Epidermal Growth Factor Receptor Regulates Interaction of the Human DF3/MUC1 Carcinoma Agent with c-Src and β-Catenin," *J. Biol. Chem.*, 276(38): 35239-35242 (2001).
Tsang et al., "A Human Cytotoxic T-Lymphocyte Epitope and Its Agonist Epitope from the Nonvariable Number of Tandem Repeat Sequence of MUC-1," *Clin. Cancer Res.*, 10: 2139-2149 (2004).
Tucker et al., "Identification and characterization of a cytotoxic T-lymphocyte agonist epitope of brachyury, a transcription factor involved in epithelial to mesenchymal transition and metastasis," *Cancer Immunol. Immunother.*, 63(12): 1307-1317 (2014).
Wei et al., "Human Mucin 1 Oncoprotein Represses Transcription of the p53 Tumor Suppressor Gene," *Cancer Res.*, 67: 1853-1858 (2007).
Written Opinion of the International Searching Authority, Application No. PCT/US2016/045289, dated Nov. 2, 2016.

*Primary Examiner* — Gary B Nickol
*Assistant Examiner* — Lakia J Jackson-Tongue
(74) *Attorney, Agent, or Firm* — Leydig, Voit & Mayer, Ltd.

(57) ABSTRACT

The invention provides Brachyury deletion mutant polypeptides, nucleic acids encoding the polypeptides, non-yeast vectors comprising the nucleic acids, non-yeast cells, and methods of use.

Figure 1:
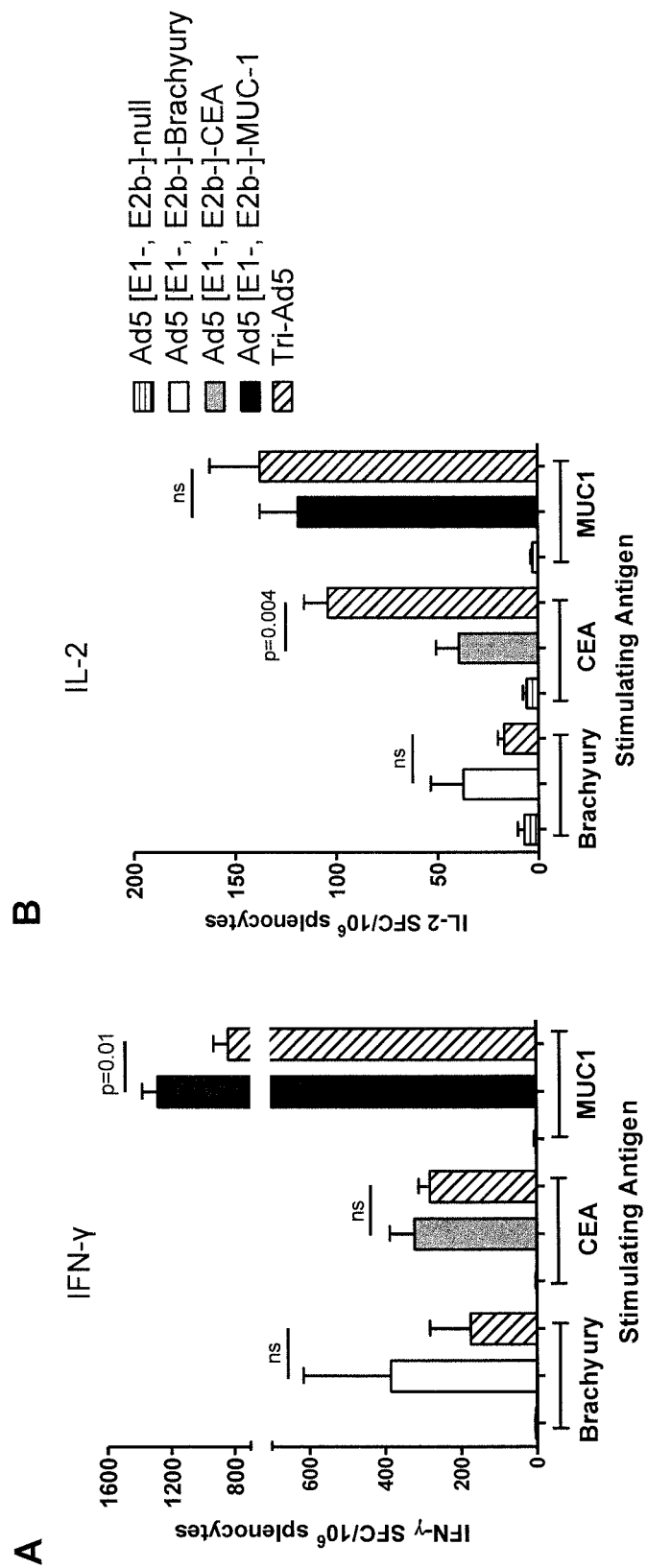

18 Claims, 4 Drawing Sheets
Specification includes a Sequence Listing.

BRACHYURY DELETION MUTANTS, NON-YEAST VECTORS ENCODING BRACHYURY DELETION MUTANTS, AND THEIR USE

CROSS-REFERENCE TO RELATED APPLICATIONS

This patent application is the U.S. National Phase of International Patent Application No. PCT/US2016/045289, filed Aug. 3, 2016, which claims the benefit of U.S. Provisional Patent Application No. 62/200,438, filed Aug. 3, 2015, each of which is incorporated by reference in its entirety herein.

STATEMENT REGARDING FEDERALLY SPONSORED RESEARCH OR DEVELOPMENT

This invention was made with Government support under project number Z01 BC010937 by the National Institutes of Health, National Cancer Institute. The Government has certain rights in the invention.

SEQUENCE LISTING

Incorporated by reference in its entirety herein is a nucleotide/amino acid sequence listing submitted concurrently herewith and identified as follows: One 12,550 Byte ASCII (Text) file named "737846 ST25.txt" created Jan. 31, 2018.

BACKGROUND OF THE INVENTION

The Brachyury gene was initially cloned from mouse developmental mutants characterized by an arrest in mesoderm formation (Heimann et al, Nature 1990; 343:617-22) has been recognized as gene that is important in mesoderm development during gastrulation. Brachyury is a member of a family of transcription factors, designated T-box transcription factors; these factors are characterized by a conserved DNA-binding domain (Papaioannou et al., Bioessays 1998; 20:9-19). These transcription factors play an essential role in the formation and organization of mesoderm in vertebrates (see, for example, Edwards et al., Genome Res 1996; 6:226-33). In addition to the important role of the T-box proteins in the control of developmental processes, several members of this family are deregulated in cancer. For example, the human Tbx2 gene has been reported to be amplified in pancreatic cancer cell lines (Mahlamaki et al., Genes Chromosomes Cancer 2002; 35:353-8) and is overexpressed in BRCA-1- and BRCA-2-mutated breast tumors (Sinclair et al., Cancer Res 2002; 62:3587-91). In addition, Tbx3 expression has been shown to be augmented in certain human breast cancer cell lines (Fan et al., Cancer Res 2004; 64:5132-9). Expression of Brachyury has also been documented in human teratocarcinoma lines: a subset of germ cell tumors, teratocarcinomas are embryonal carcinoma cells with competence for mesoderm differentiation (Gokhale et al., Cell Growth Differ 2000; 11:157-62) and in chordomas (see, for example, Vojovic et al., J Pathol 2006; 209:157-65). Brachyury also is overexpressed in a variety of human carcinomas, including breast, lung, colon, prostate and hepatocellular carcinoma and in malignancies of B-cell origin, such as chronic lymphocytic leukemia (CLL), B-cell lymphomas and Multiple Myeloma, among others.

Immunotherapeutic interventions against cancer depend on the identification of tumor antigens able to elicit a host immune response against the tumor cells. Good targets are molecules that are selectively expressed by malignant cells and that are also essential for malignant transformation and/or tumor progression. A need remains for reagents that induce an effective immune response to cancer, including a CD4 and a CD8 T cell response.

BRIEF SUMMARY OF THE INVENTION

The invention provides Brachyury deletion mutant polypeptides and, in particular, the invention provides a polypeptide comprising, consisting essentially of, or consisting of the amino acid sequence of SEQ ID NO: 3.

The invention also provides nucleic acids encoding the polypeptides, non-yeast vectors comprising the nucleic acids, cells, and compositions thereof, as well as methods of use.

In particular, the invention provides a method for inducing an immune response to Brachyury comprising administering to a subject an effective amount of the polypeptide, nucleic acid, non-yeast vector, cell, or composition the composition, thereby inducing the immune response, wherein the immune response comprises a Brachyury specific CD4+ T cell response.

The invention provides a method for treating or preventing cancer in a subject, comprising administering to the subject an effective amount of the polypeptide, nucleic acid, non-yeast vector, cell, or composition the composition, thereby treating or preventing the cancer in the subject.

The invention also provides a method for inhibiting the growth of a cancer cell in a subject, the method comprising contacting a dendritic cell with the polypeptide to produce a specific antigen presenting cell; and administering the specific antigen presenting cell to the subject, thereby inducing an immune response and inhibiting the growth of the cancer cell.

BRIEF DESCRIPTION OF THE SEVERAL VIEWS OF THE DRAWING(S)

FIGS. 1A and 1B are graphs depicting an analysis of IFN-γ- and IL-2-expressing splenocytes, respectively, following vaccination of mice with Ad5 [E 1-, E2b-]-Brachyury, Ad5 [E1-, E2b-]-CEA, Ad5 [E1-, E2b-]-MUC1, Tri-Ad5, and Ad5 [E1-, E2b-]-null. C57B1/6 mice (n=5/group) were vaccinated three times at 2-week intervals with $10^{10}$ VP (viral particle) of Ad5 [E1-, E2b-]-Brachyury (white bar), Ad5 [E1-,E2-]-CEA (grey bar), Ad5 [E1-, E2b-]-MUC1 (black bar) or Tri-Ad5 (1:1:1 mixture of $10^{10}$ VP each of Ad5 [E1-, E2b-]-Brachyury, Ad5 [E1-, E2b-]-CEA, Ad5 [E1-, E2b-]-MUC1) (diagonal hatched bar). Controls received $3 \times 10^{10}$ VP of Adeno-null (horizontal striped bar). Splenocytes were collected 14 days after the final vaccination and assessed for IFN-γ-secreting cells (A) or IL-2-secreting cells (B) by ELISPOT assay. For positive controls, splenocytes were exposed to Concanavalin A (Con A). Data reported as the number of spot forming cells (SPFs) per $10^6$ splenocytes. The error bars depict the SEM. Significant differences (p<0.05) between columns are reported in p-values, not significant=ns.

FIGS. 2A-D are graphs depicting an analysis of CD8+ and CD4+ and multifunctional cellular populations following vaccination with Ad5 [E1-, E2b-]-Brachyury, Ad5 [E1-, E2b-]-CEA, Ad5 [E1-, E2b-]-MUC1, Tri-Ad5, and Ad5 [E1-, E2b-]-null. C57B1/6 mice (n=5/group) were vaccinated three times at 2-week intervals with $10^{10}$ VP (viral particle) of Ad5 [E1-, E2b-]-Brachyury (white bar), Ad5

[E1-, E2b-]-CEA (grey bar), Ad5 [E1-, E2b-]-MUC1 (black bar) or Tri-Ad5 (1:1:1 mixture of $10^{10}$ VP (viral particle) each of Ad5 [E1-, E2b-]-Brachyury, Ad5 [E1-, E2b-]-CEA, Ad5 [E1-, E2b-]-MUC1) (diagonal hatched bar). Controls received $3\times10^{10}$ VP of Ad5 [E1-, E2b-]-null (horizontal striped bar). Splenocytes were collected 14 days after the final vaccination and were assessed by FACS for $CD8\alpha^+$ (A) and $CD4^+$ (B) IFN-γ-expressing cells, or for $CD8\alpha^+$ (C) and $CD4^+$ (D) cells secreting IFN-γ and TNF-α. For positive controls, splenocytes were exposed to Concanavalin A (Con A). The error bars depict the SEM. Significant differences (p<0.05) between columns are reported in p-values, not significant=ns.

Figure 3:
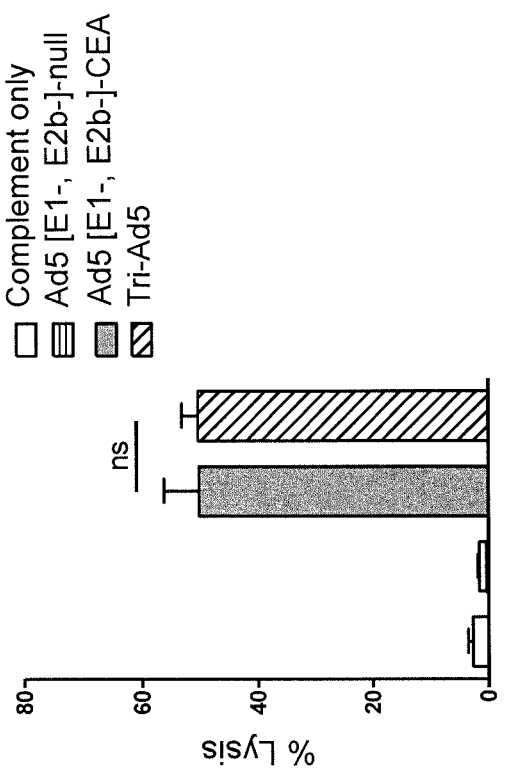
Figure 3:
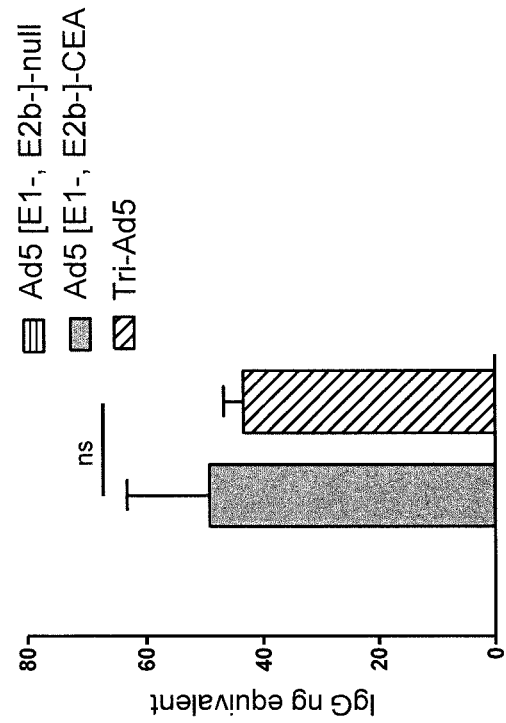

FIGS. 3A and 3B are graphs depicting CEA antibody activity from sera from mice vaccinated with Ad5 [E1-, E2b-]-CEA or Tri-Ad5. CEA IgG levels in mice vaccinated three times with $10^{10}$ VP (viral particle) of Ad5 [E1-, E2b-]-CEA (grey bar), Tri-Ad5 (diagonal hatched bar) or $3\times10^{10}$ VP of Ad5 [E1-, E2b-]-null (horizontal striped bar) were determined by ELISA (A). Complement-dependent cytotoxicity (CDC) against MC38-CEA2 cells was performed (B). The error bars depict the SEM. Significant differences (p<0.05) between columns are reported in p-values, not significant=ns.

Figure 4:
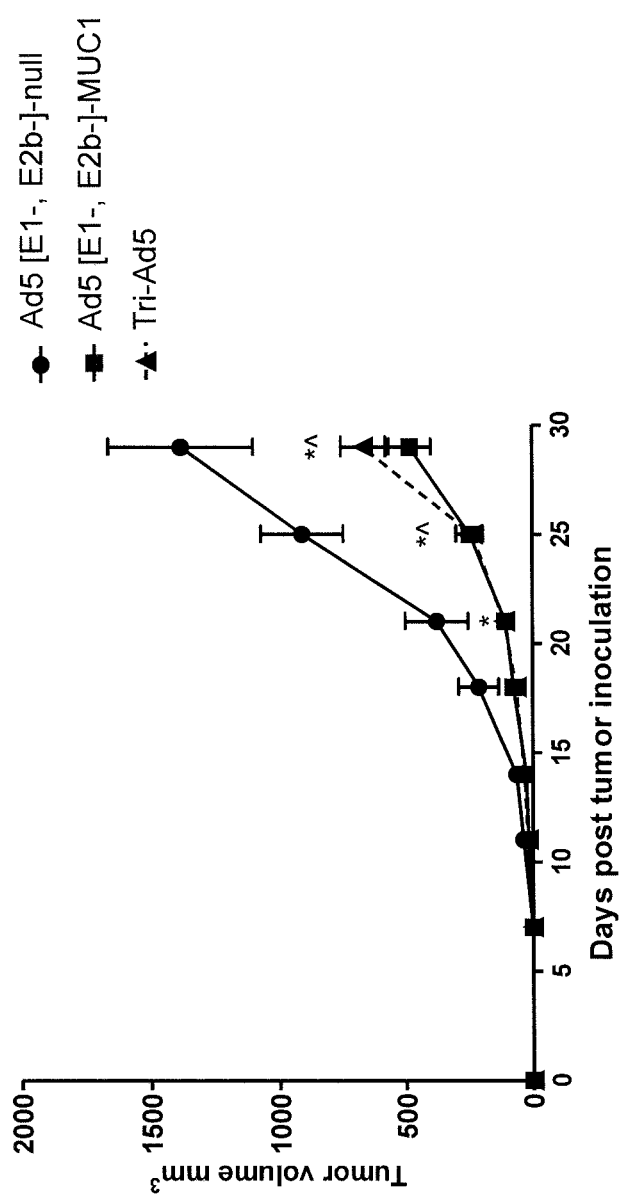

FIG. 4 is a graph depicting a comparison of immunotherapy of MUC1-expressing tumors using Ad5 [E1-, E2b-]-MUC1 vs Tri-Ad5. C57B1/6 mice (n=7/group) were inoculated with $10^6$ MC-38-MUC1 cells subcutaneously in the left flank. Mice were administered $10^{10}$ VP (viral particle) of Ad5 [E1-, E2b-]-MUC1 or Tri-Ad5 (1:1:1 mixture of $10^{10}$ VP each of Ad5 [E1-, E2b-]-CEA, Ad5 [E1-, E2b-]-MUC1, and Ad5 [E1-, E2b-]-Brachyury, $3\times10^{10}$ VP total). A control group of mice received $3\times10^{10}$ VP of Ad5 [E1-, E2b-]-null (no transgene). Tumor growth was monitored and volumes calculated. (*) indicates days when Ad5 [E1-, E2b-]-MUC1 treated mice had significantly smaller (p<0.05) tumors than control mice and (^) indicates days when Tri-Ad5-treated mice had significantly smaller (p<0.05) tumors than control mice. There was no significant difference (p>0.1) between Ad5 [E1-, E2b-]-MUC1 vs. Tri-Ad5-treated mice at any time point. Error bars represent the SEM.

DETAILED DESCRIPTION OF THE INVENTION

Brachyury (also known as "T-protein") is a protein which is transcribed in the mesoderm. Full-length Brachyury protein has the amino acid sequence of SEQ ID NO: 1 (see also GENBANK® Accession No NP_003172 and GENBANK® Accession No. NM_003181). Full length Brachyury protein with an agonist epitope has the amino acid sequence of SEQ ID NO: 2.

The invention provides a modified Brachyury polypeptide comprising a modification wherein the DNA binding activity of the Brachyury protein has been reduced or abolished by mutation (e.g., by deletion, substitution, insertion or other modification of the Brachyury DNA binding region sufficient to reduce or abolish the natural DNA binding activity of the Brachyury protein).

In one embodiment, the invention provides a Brachyury deletion mutant, wherein the sequence has been modified to delete a fragment of 25 amino acids involved in DNA binding (DNA binding domain). The DNA binding domain corresponds to residues 198-222 of SEQ ID NO: 1 and SEQ ID NO: 2.

In one embodiment of the invention, the Brachyury deletion mutant is a polypeptide comprising, consisting essentially of, or consisting of the amino acid sequence of SEQ ID NO: 3, wherein residue 228 can be Ser or Val. The polypeptide of SEQ ID NO: 3 is one example of a Brachyury deletion mutant, where the amino acid sequence differs from the amino acid sequence of the human Brachyury protein of SEQ ID NO: 1 by deletion of positions 198-222 (i.e., positions 198-222 of SEQ ID NO: 1 or 2 are not present in SEQ ID NO: 3). SEQ ID NO: 3 is a polypeptide consisting of positions 1-197 fused directly to positions 223-435 of SEQ ID NO: 1 or 2. This Brachyury deletion mutant has disrupted DNA binding ability as compared to the Brachyury protein of SEQ ID NO: 3.

In some embodiments, the Brachyury deletion mutant polypeptide comprises an amino acid sequence at least 95% identical, at least 96% identical, at least 97% identical, at least 98% identical, at least 99%, to the amino acid sequence of SEQ ID NO: 3. In other embodiments, the Brachyury deletion mutant polypeptide comprises, or consists of, the amino acid sequence of SEQ ID NO: 3, the amino acid sequence of SEQ ID NO: 3 without the N-terminal methionine, and/or the amino acid sequence of SEQ ID NO: 3 with substitutions at position 177 (Asp vs. Gly, respectively), position 343 (Thr vs. Ser, respectively) and position 384 (Asn vs. Asp, respectively).

The polypeptide can be prepared by any method, such as by synthesizing the polypeptide or by expressing a nucleic acid encoding an appropriate amino acid sequence in a cell and harvesting the polypeptide from the cell. A combination of such methods also can be used. Methods of de novo synthesizing polypeptides and methods of recombinantly producing polypeptides are known in the art (see, e.g., Chan et al., *Fmoc Solid Phase polypeptide Synthesis*, Oxford University Press, Oxford, United Kingdom, 2005; polypeptide *and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994).

The polypeptide can be in the foul' of a fusion protein (e.g., a fusion protein comprising the polypeptide and one or more additional active agents and/or tags). The polypeptide also can be linked to a carrier. Generally, a carrier is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., PNAS 96:5194-97, 1999; Lee et al., J. Immunol. 116:1711-18, 1976; Dintzis et al., PNAS 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Suitable carriers include, but are not limited to, a hepatitis B small envelope protein HBsAg. This protein has the capacity to self-assemble into aggregates and can form viral-like particles. The preparation of HBsAg is well documented, see for example European Patent Application Publication No. EP-A-0 226 846, European Patent Application Publication No. EP-A-0 299 108 and PCT Publication No. WO 01/117554, and the amino acid sequence disclosed, for example, in Tiollais et al., Nature, 317: 489, 1985, and European Patent Publication No. EP-A-0 278 940, and PCT Publication No. WO 91/14703.

The invention also provides a nucleic acid encoding the polypeptide or fusion protein. The nucleic acid can comprise DNA, cDNA, and/or RNA, can be single or double stranded, and can be naturally-occurring, synthetic, and/or recombinant. Furthermore, the nucleic acid can comprise nucleotide analogues or derivatives (e.g., inosine or phophorothioate nucleotides and the like). Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. Freeman and Co., NY).

The nucleic acid can encode the polypeptide alone or as part of a fusion protein. The nucleic acid encoding the polypeptide can be provided as part of a construct comprising the nucleic acid and elements that enable delivery of the nucleic acid to a cell, and/or expression of the nucleic acid in a cell. For example, the polynucleotide sequence encoding the polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. Suitable promoters include, but are not limited to, an SV40 early promoter, RSV promoter, adenovirus major late promoter, human CMV immediate early I promoter, poxvirus promoter, 30K promoter, I3 promoter, sE/L promoter, 7.5K promoter, 40K promoter, and C1 promoter. T DNA vaccines are described in U.S. Pat. Nos. 5,589,466; 5,973,972, which are each incorporated herein by reference. In addition to the delivery protocols described in those applications, alternative methods of delivering DNA are described in U.S. Pat. Nos. 4,945,050 and 5,036,006.

A nucleic acid encoding the polypeptide or fusion protein can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the polypeptide can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., Cold Spring Harbor Symp. Quant. Biol. 51:263, 1987; and Erlich, ed., PCR Technology, (Stockton Press, NY, 1989). Polynucleotides also can be isolated by screening genomic or cDNA libraries with probes selected from the sequences of the desired polynucleotide under stringent hybridization conditions.

The invention further provides a non-yeast vector comprising the nucleic acid. Examples of suitable vectors include plasmids (e.g., DNA plasmids), bacterial vectors, and viral vectors, such as poxvirus, retrovirus, adenovirus, adeno-associated virus, herpes virus, polio virus, alphavirus, baculorvirus, and Sindbis virus. When the vector is a plasmid (e.g., DNA plasmid), the plasmid can be complexed with chitosan.

Bacterial Vectors: The vector can be a bacterial vector, such as a *Listeria* or *Salmonella* vector. *Listeria* is a Gram-positive bacilli. The genus *Listeria* currently contains seven species: *L. grayi, L. innocua, L. ivanovii, L. monocytogenes, L. murrayi, L. seeligeri,* and *L. welshimeri. L. monocytogenes* is an intracellular bacterium that has been used as a vector to deliver genes in vitro.

*Salmonella* is a genus of rod-shaped, Gram-negative, non-spore-forming, predominantly motile enterobacteria with diameters around 0.7 to 1.5 μm, lengths from 2 to 5 μm, and flagella which grade in all directions (i.e. peritrichous). They are chemoorganotrophs, obtaining their energy from oxidation and reduction reactions using organic sources, and are facultative anaerobes. *Salmonella* can be used as delivery vector for therapeutic proteins, by including plasmids, such as those with truncated tetA genes in the host cell. Attenuated *S. typhimirium* can be transformed with DNA plasmids, such as, but not limited to, pIRES (Invitrogen) and used as a carrier for delivery of polypeptides and proteins.

Poxvirus: The vector can be a poxvirus selected from the group consisting of orthopox, avipox, fowlpox, raccoon pox, rabbit pox, capripox (e.g., goat pox and sheep pox), leporipox, and suipox (e.g., swinepox). Examples of avipox viruses include fowlpox, pigeonpox, and canarypox, such as ALVAC. Examples of orthopox viruses include vaccinia, modified vaccinia Ankara (MVA), Wyeth, NYVAC, TROYVAC, Dry-Vax, PDXVAC-TC (Schering-Plough Corporation), and derivatives thereof. For example, derivatives of the Wyeth strain include, but are not limited to, derivatives which lack a functional K1L gene.

Exemplary pox viral vectors for expression as described for example, in U.S. Pat. No. 6,165,460. The vaccinia virus genome is known in the art. It is composed of a HIND F13L region, TK region, and an HA region. Recombinant vaccinia virus has been used to incorporate an exogenous gene for expression of the exogenous gene product (see, for example, Perkus et al. *Science* 229:981-984, 1985; Kaufman et al. *Int. J. Cancer* 48:900-907, 1991; Moss *Science* 252:1662, 1991). Baxby and Paoletti (*Vaccine* 10:8-9, 1992) disclose the construction and use as a vector, of the non-replicating poxvirus, including canarypox virus, fowlpox virus and other avian species. Sutter and Moss (*Proc. Nat'l. Acad. Sci U.S.A.* 89:10847-10851, 1992) and Sutter et al. (*Virology* 1994) disclose the construction and use as a vector, the non-replicating recombinant Ankara virus (MVA, modified vaccinia Ankara) in the construction and use of a vector.

Plasmids: Plasmids have been designed with a number of goals in mind, such as achieving regulated high copy number and avoiding potential causes of plasmid instability in bacteria, and providing means for plasmid selection that are compatible with human therapeutic use. Particular attention has been paid to the dual requirements of gene therapy plasmids. First, they are suitable for maintenance and fermentation in E. coli, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids that encode the polypeptide are composed of: (1) a high copy number replication origin, (2) a selectable marker, such as, but not limited to, the neo gene for antibiotic selection with kanamycin, (3) transcription termination sequences, and (4) a multicloning site for incorporation of various nucleic acid cassettes; and (5) a nucleic acid sequence encoding the polypeptide.

There are numerous plasmid vectors that are known in the art for inducing a nucleic acid encoding a polypeptide. These include, but are not limited to, the vectors disclosed in U.S. Pat. Nos. 6,103,470; 7,598,364; 7,989,425; and 6,416,998.

Adenovirus Vectors: Adenovirus vectors (Ad) vectors can be produced that encode a Brachyury protein or a Brachyury polypeptide and are of use in the methods disclosed herein. These vectors are of use in the methods disclosed herein, including replication competent, replication deficient, gutless forms thereof, and adeno-associated virus (AAV) vectors. Without being bound by theory, adenovirus vectors are known to exhibit strong expression in vitro, excellent titer, and the ability to transduce dividing and non-dividing cells in vivo (Hitt et al., Adv in Virus Res 55:479-505, 2000). When used in vivo these vectors lead to strong but transient gene expression due to immune responses elicited to the vector backbone.

Adenoviral vectors are often constructed by insertion of a nucleic acid encoding a Brachyury protein in place of, or in the middle of, essential viral sequences such as those found at the E1 region of adenovirus (Berkner, BioTechniques, 6:616-629, 1988; Graham et al., Methods in Molecular Biology, 7:109-128, Ed: Murcy, The Human Press Inc., 1991). Inactivation of essential viral genes by, for example, deletion or insertion, disables the adenovirus' ability to replicate. To propagate such vectors in cell culture, the deleted genes must be provided in trans (for example, the E1A and E1B proteins in the case of an E1 delete vector). These replication-defective adenoviruses are produced in packaging cells engineered to complement the replication-incompetent virus by expressing the subset of genetic elements deleted from their viral genome. Potential sites for the insertion of a nucleic acid of interest, such as a nucleic acid encoding a Brachyury protein, in recombinant adenoviral vectors include, without limitation, the E1, E2, E3 and the E4 region. In some embodiments, a recombinant adenoviral vector is produced from a human adenovirus that has the E1 region deleted and replaced with a nucleic acid encoding a Brachyury protein or Brachyury polypeptide. The resulting viral vector, with one or more of its essential genes inactivated, is replication defective (Statford-Perricaudet et al., Human Gene Therapy, 1:241-256, 1990).

The recombinant adenovirus vectors can include: (1) a packaging site enabling the vector to be incorporated into replication-defective Ad virions; and (2) the nucleic acid encoding the polypeptide. Other elements of use for incorporation into infectious virions, include the 5' and 3' Ad ITRs; the E2 and E3 genes can be included in the vector. In some embodiments, a nucleic acid encoding the polypeptide is inserted into adenovirus in the deleted E1A, E1B or E3 region of the virus genome. In some embodiments, the adenovirus vectors do not express one or more wild-type adenovirus gene products, such as E1a, E1b, E2, E3, E4. In some non-limiting examples, virions are typically used together with packaging cell lines that complement the functions of E1, E2A, E4 and optionally the E3 gene regions (see, for example, U.S. Pat. Nos. 5,872,005, 5,994,106, 6,133,028 and 6,127,175). In one embodiment, the adenovirus serotype 5 (Ad5) vector gene delivery platform (Ad5 [E1-, E2b-]) described in the examples in which regions of the early 1 (E1), early 2 (E2b), and early 3 (E3) genes have been deleted can be used. Adenovirus vectors can be purified and formulated using techniques known in the art.

In some embodiments, packaging cell lines such as the human embryonic kidney 293 ("HEK-293" or "293") cell line (Graham et al., J. Gen. Virol., 36:59-72, 1977) or human embryonic retinoblast ("HER-911" or "911") cell line (Fallaux et al., Hum. Gene Ther., 7:215-222, 1996), provide in trans the missing region, such as the E1 region, so that the deleted or modified adenoviral vector can replicate in such cells. Suitable adenoviral vectors are disclosed, for example, in U.S. Patent Publication No. 20080193484, which is incorporated herein by reference. Replication-defective adenovirus virions encapsulating the recombinant adenovirus vectors can be made by standard techniques known in the art using packaging cells and packaging technology. Examples of these methods can be found, for example, in U.S. Pat. No. 5,872,005, incorporated herein by reference in its entirety.

Adeno-Associated Vectors (AAV): Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

Recombinant AAV (rAAV) virions can be constructed such that they include, as operatively linked components in the direction of transcription, control sequences including transcriptional initiation and termination sequences, and the nucleic acid encoding the polypeptide. These components are bounded on the 5' and 3' end by functional AAV inverted terminal repeat (ITR) sequences. By "functional AAV ITR sequences" is meant that the ITR sequences function as intended for the rescue, replication and packaging of the AAV virion. Hence, AAV ITRs for use in the vectors need not have a wild-type nucleotide sequence, and can be altered by the insertion, deletion or substitution of nucleotides, or the AAV ITRs can be derived from any of several AAV serotypes, provided they are functional. An AAV vector is a vector derived from an adeno-associated virus serotype, including without limitation, AAV-1, AAV-2, AAV-3, AAV-4, AAV-5, AAV-6, AAV-7, AAV-8, etc. In some embodiments, the AAV vectors have the wild type REP and CAP genes deleted in whole or part, but retain functional flanking ITR sequences. These vectors can all be used, without limitation, for the expression of a Brachyury protein.

Alphavirus: Alphaviruses encoding the polypeptide are provided and are of use in the methods disclosed herein. Alphaviruses are a set of serologically related arthropod-borne viruses of the Togavirus family. Twenty-six known viruses and virus subtypes have been classified within the alphavirus genus utilizing the hemagglutination inhibition (HI) assay. Briefly, the HI test segregates the 26 alphaviruses into three major complexes: the Venezuelan encephalitis (VE) complex, the Semliki Forest (SF) complex, and the western encephalitis (WE) complex. In addition, four additional viruses, eastern encephalitis (EE), Barmah Forest, Middelburg, and Ndumu, receive individual classification based on the HI serological assay. Representative examples of suitable alphaviruses include Aura (American Type Culture Collection (ATCC) VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69), Venezuelan equine encephalomyelitis virus (ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375), see U.S. Pat. No. 5,843,723, which is incorporated herein by reference.

In some embodiments, and alphavirus vector is a Sinbis virus. In some embodiments, recombinant alphavirus vector constructs are utilized that include a 5' sequence which is capable of initiating transcription of an alphavirus, a nucleotide sequence encoding alphavirus nonstructural proteins, a viral junction region which has been inactivated such that viral transcription of the subgenomic fragment is prevented, an alphavirus RNA polymerase recognition sequence, and a nucleic acid sequence encoding the polypeptide. Alphavirus vector constructs which have inactivated viral junction regions do not transcribe the subgenomic fragment, making them suitable for a wide variety of applications.

In some embodiments, the alphavirus such as Sinbis virus, constructs are provided which contain a 5' promoter which is capable of initiating the synthesis of viral RNA in vitro from cDNA. The 5' promoters include both eukaryotic and prokaryotic promoters, such as, for example, the β-galactosidase promoter, trpE promoter, lacZ promoter, T7 promoter, T3 promoter, SP6 promoter, SV40 promoter, CMV promoter, and MoMLV LTR. Representative examples of such sequences include nucleotides 1-60, and to a lesser extent nucleotides 150-210, of the wild-type Sindbis virus, nucleotides 10-75 for tRNA Asparagine (Schlesinger et al., U.S. Pat. No. 5,091,309), and 5' sequences from other Togaviruses which initiate transcription.

Alphavirus vectors can contain sequences which encode alphavirus nonstructural proteins (NSPs). As an example, for Sindbis virus there are four nonstructural proteins, NSP1, NSP2, NSP3 and NSP4, which encode proteins that enable the virus to self-replicate. Nonstructural proteins 1 through 3 (NSP1-NSP3) are, encoded by nucleotides 60 to 5750 of the wild-type Sindbis virus. These proteins are produced as a polyprotein and later cleaved into nonstructural proteins NSP1, NSP2, and NSP3. NSP4. The alphavirus vector constructs can also include a viral junction region which has been inactivated, such that viral transcription of the subgenomic fragment is prevented. Briefly, the alphavirus viral junction region normally controls transcription initiation of the subgenomic mRNA. In the case of the Sindbis virus, the normal viral junction region typically begins at approximately nucleotide number 7579 and continues through at least nucleotide number 7612 (and possibly beyond), see U.S. Pat. No. 5,843,723 for the complete sequence, incorporated herein by reference.

Several members of the alphavirus genus can be used as "replicon" expression vectors. Replicon vectors may be utilized in any of several formats, including DNA vector constructs, RNA replicon vectors, and recombinant replicon particles (see below). These include, for example, SIN (Xiong et al., Science 243:1188-1191, 1989; Dubensky et al., J. Virol. 70:508-519, 1996; Hariharan et al., J. Virol. 72:950-958, 1998; Polo et al., PNAS 96:4598-4603, 1999), Semliki Forest virus (Liljestrom, Bio/Technology 9:1356-1361,1991; Berglund et al., Nat. Biotech. 16:562-565, 1998), VEE (Pushko et al. Virology 239:389-401, 1997), and chimeras of multiple alphaviruses (U.S. Pat. No. 6,376,236; PCT Publication No. WO2002099035; Perri et al., J. Virol. 77:10394-10403, 2003).

Alphavirus vector constructs are also disclosed in U.S. Pat. Nos. 5,789,245; 5,843,723; 5,814,482, and 6,015,694; PCT Publication No. WO 00/61772; and PCT Publication No. WO 02/99035. Generally, these vectors include a 5' sequence which initiates transcription of alphavirus RNA, a nucleotide sequence encoding alphavirus nonstructural proteins, a viral subgenomic junction region promoter which directs the expression of an adjacent heterologous nucleic acid sequence, an RNA polymerase recognition sequence and a polyadenylate tract.

An alphavirus can be used as a replicon (a recombinant alphavirus particle) that is a virus-like particle containing a self-replicating alphavirus vector or "replicon" nucleic acid. The replicon particle itself is generally considered to be replication incompetent or "defective," that is no progeny replicon particles will result when a host cell is infected with a replicon particle, because genes encoding one or more structural proteins necessary for packaging are deleted.

Although alphavirus vectors can be used directly for administration in vivo as RNA, or delivered as a plasmid-based cDNA (e.g., Eukaryotic Layered Vector Initiation System), often, for in vivo vaccine and therapeutic applications, the alphavirus RNA replicon vector or replicon RNA is first packaged into a virus-like particle, comprising alphavirus structural proteins (e.g., capsid protein and envelope glycoproteins). Alphavirus and replicons of use are disclosed, for example, in Published U.S. Patent Application No. 20110002958, which is incorporated herein by reference. Because of their configuration, vector replicons do not express these alphavirus structural proteins necessary for packaging into recombinant alphavirus replicon particles. Thus, to generate replicon particles, the structural proteins must be provided in trans.

Packaging can be accomplished by a variety of methods, including transient approaches such as co-transfection of in vitro transcribed replicon and defective helper RNA(s) (Liljestrom, Bio/Technology 9:1356-1361, 1991; Bredenbeek et al., I Virol. 67:6439-6446, 1993; Frolov et al., J. Virol. 71:2819-2829, 1997; Pushko et al., Virology 239:389-401, 1997; U.S. Pat. Nos. 5,789,245 and 5,842,723) or plasmid DNA-based replicon and defective helper constructs (Dubensky et al., J. Virol. 70:508-519, 1996), as well as introduction of alphavirus replicons into stable packaging cell lines (PCL) (Polo et al., PNAS 96:4598-4603, 1999; U.S. Pat. Nos. 5,789,245; 5,842,723; 6,015,694).

The trans packaging methodologies permit the modification of one or more structural protein genes (for example, to incorporate sequences of alphavirus variants such as the attenuated mutants, see U.S. Pat. Nos. 5,789,245; 5,842,723; 6,015,694), followed by the subsequent incorporation of the modified structural protein into the final replicon particles. In addition, such packaging permits the overall modification of alphavirus replicon particles by packaging of a vector construct or RNA replicon derived from a first alphavirus using structural proteins derived from a second alphavirus different from that of the vector construct.

Measles Virus: Measles viruses encoding the polypeptide are provided and are of use in the methods disclosed herein. The nucleic acid sequences of Measles Viruses are disclosed in PCT Publication No. WO 98/13501, which provides the sequence of a DNA copy of the positive strand (antigenomic) message sense RNA of various wild-type of vaccine measles strains, including Edmonston Wild-type strain, Moraten strain and Schwarz strain. PCT Publication No. WO 97/06270, incorporated herein by reference, discloses the production of recombinant measles vectors.

An attenuated strain of measles virus can also be used to deliver the polypeptide. The Moraten attenuated form of the virus has been used world-wide as a vaccine and has an excellent safety record (Hilleman, et al., J. Am. Med. Assoc. 206: 587-590, 1968). Accordingly, in one embodiment, the Moraten strain is used. The Moraten vaccine is commercially available from MERCK® and is provided lyophilized in a vial which when reconstituted to 0.5 ml comprises $10^3$ pfu/ml.

In a further embodiment, the Edmonston-B vaccine strain of measles virus is used (MV-Edm) (Enders and Peebles, Proc. Soc. Exp. Biol. Med. 86: 277-286, 1954). MV-Edm grows efficiently in tumor cells but its growth is severely restricted in primary cultures of human peripheral blood mononuclear cells, normal dermal fibroblasts, and vascular smooth muscle cells. A form of the Enders attenuated Edmonston strain is available commercially from Merck (ATTENUVAX®). Other attenuated measles virus strains can also be utilized, such as Leningrad-16, and Moscow-5 strains (Sinitsyna, et al., Res. Virol. 141(5): 517-31, 1990), Schwarz strain (Fourier, et al., Pediatric 24(1): 97-8, 1969), 9301B strain (Takeda, et al. J. VIROL. 72/11: 8690-8696), the AIK-C strain (Takehara, et al., Virus Res 26 (2): 167-75, 1992), and those described in Schneider-Shaulies, et al., PNAS 92(2): 3943-7, 1995).

In some embodiments, the recombinant measles virus nucleotide sequence comprises a replicon having a total number of nucleotides which is a multiple of six. The "rule of six" is expressed in the fact that the total number of nucleotides present in the recombinant cDNA finally amount to a total number of nucleotides which is a multiple of six, a rule which allows efficient replication of genome RNA of the measles virus.

In additional embodiments, heterologous DNA, such as a nucleic acid encoding Brachyury protein, is cloned in the measles virus within an Additional Transcription Unit (ATU) inserted in the cDNA corresponding to the antigenomic RNA of measles virus. The location of the ATU can vary along the cDNA: it is however located in such a site that it will benefit from the expression gradient of the measles virus. Therefore, the ATU can be spread along the cDNA. In one embodiment, the ATU is inserted in the N-terminal portion of the sequence and especially within the region upstream from the L-gene of the measles virus and upstream from the M gene of the virus. In other embodiments, the ATU is inserted upstream from the N gene of the virus, see U.S. Published Patent Application No. 2011/0129493, incorporated herein by reference. Particular cistrons in the measles virus genome can targeted to modify genes whose expression is associated with attenuation (Schneider-Shaulies et at. PNAS 92(2): 3943-7, 1995; Takeda, et al. J. Virol. 72/11: 8690-8696, 1998). Thus, in one embodiment, a recombinant measles virus strain is generated encoding the polypeptide in any of an H protein, a V protein, a C protein, and combinations thereof.

Recombinant measles virus vectors include the plasmid pTM-MVSchw which contains the cDNA resulting from reverse transcription of the antigenomic RNA of measles virus and an adapted expression control sequence including a promoter and terminator for the T7 polymerase. Vectors are also disclosed, for example, in U.S. Published Patent Application No. 2006/0013826. These vectors are of use in the methods disclosed herein.

Additional attenuated strains of measles virus can be produced that express the polypeptide. Attenuated strains of viruses are obtained by serial passage of the virus in cell culture (e.g., in non-human cells), until a virus is identified which is immunogenic but not pathogenic. While wild type virus will cause fatal infection in marmosets, vaccine strains do not. Individuals receiving an attenuated measles virus vaccine do not display classical measles symptoms. Attenuation is associated with decreased viral replication (as measured in vivo by inability to cause measles in monkeys), diminished viremia, and failure to induce cytopathological effects in tissues (e.g., cell-cell fusion, multinucleated cells). See U.S. Pat. No. 7,393,527.

In one embodiment, an effective dose of an attenuated measles virus encoding the polypeptide is produced by infecting a primary cell or a continuous cell line with a starting innoculum of a stock comprising an attenuated Moraten strain of measles virus (or an innoculum of an MMR stock) or the MV-Edm strain or any of the other strains described above and expanding the virus after serial passage. Cells or cell lines include, but are not limited to, monkey kidney or testes cells or monkey cell lines (e.g., Vero, KB, CV-1, BSC-1, and the like). Viral replication in cells is observed as cell-cell fusion and syncytia formation.

The attenuated measles virus is expanded until a desired dose concentration is obtained in standard cell culture media. In one embodiment, the therapeutically effective dose concentration is about $10^3$ to $10^{12}$ pfu. In another embodiment of the invention, the concentration is about $10^5$ to $10^8$ pfu. Viral titer can be assayed by inoculating cells (e.g., Vero cells) in culture dishes (e.g., such as 35 mm dishes). After 2-3 hours of viral adsorption, the inoculum is removed and cells are overlaid with a mixture of cell culture medium and agarose or methylcellulose (e.g., 2 ml DMEM containing 5% FCS and 1% SeaPlaque agarose). After about 3 to about 5 days, cultures are fixed with 1 ml of 10% trifluoroacetic acid for about 1 hour, then UV cross-linked for 30 minutes. After removal of the agarose overlay, cell monolayers are stained with crystal violet and plaques are counted to determine viral titer. Virus is harvested from cell syncytia by scraping cells from the dishes, subjecting them to freeze/thawing (e.g., approximately two rounds), and centrifuging. The cleared supernatants represent "plaque purified" virus.

Viral stocks are produced by infection of cell monolayers (e.g., adsorption for about 1.5 hours at 37° C.), followed by scraping of infected cells into a suitable medium (e.g., Opti-MEM, Gibco-BRL) and freeze/thaw lysis (for example, 2 rounds). Viral stocks are aliquoted, frozen and stored at 70° C.-80° C. and can be stored at concentrations higher than the therapeutically effective dose. In one embodiment, viral stock is stored in a stabilizing solution. Stabilizing solutions are known in the art, see for example, U.S. Pat. Nos. 4,985,244, and 4,500,512.

Poliovirus: Polioviruses encoding the polypeptide are provided and are of use in the methods disclosed herein. The entire poliovirus genome has been cloned and sequenced and the viral proteins identified. An infectious poliovirus cDNA is also available which has allowed further genetic manipulation of the virus (Racaniello V R et al., Science 214(4542) 916-919, 1981). The wild-type genomic RNA molecule is 7433 nucleotides long, polyadenylated at the 3' end and has a small covalently attached viral protein (VPg) at the 5' terminus (Kitamura N et al., Nature 291:547-553; 1981 Racaniello V R et al., Proc. Natl. Acad. Sci. USA 78:4887-4891, 1981). Expression of the poliovirus genome occurs via the translation of a single protein (polyprotein) which is subsequently processed by virus encoded proteases (2A and 3C) to give the mature structural (capsid) and nonstructural proteins (Kitamura N et al., Nature 291:547-553, 1981; Koch F et al., The Molecular Biology of Poliovirus, Springer-Verlag, Vienna, 1985). Poliovirus replication is catalyzed by the virus-encoded RNA-dependent RNA polymerase, which copies the genomic RNA to give a complementary RNA molecule, which then serves as a template for further RNA production (Koch F et al., supra; Kuhn R J et al., in D J Rowlands et al. (ed.) Molecular Biology of Positive Strand RNA viruses, Academic Press Ltd., London, 1987). The translation and proteolytic processing of the poliovirus polyprotein is described in Nicklin M J H et al., Bio/Technology 4:33-42, 1986.

The viral RNA genome encodes the necessary proteins required for generation of new progeny RNA, as well as encapsidation of the new RNA genomes. In vitro, poliovirus is lytic, resulting in the complete destruction of permissive cells. Since the viral replication cycle does not include any DNA intermediates, there is no possibility of integration of viral DNA into the host chromosomal DNA.

Early studies identified three poliovirus types based on reactivity to antibodies (Koch F et al., supra, 1985). These three serological types, designated as type I, type II, and type III, have been further distinguished as having numerous nucleotide differences in both the non-coding regions and the protein coding regions. All three strains are suitable for use in delivering heterologous proteins. In addition, there are also available attenuated versions of all three strains of poliovirus.

Replicons can comprise deoxyribonucleic acid (DNA) or ribonucleic acid (RNA). Replicons are poliovirus-based polynucleotides that lack a wild type poliovirus nucleic acid necessary for encapsidation of the virus. Consequently, newly encapsidated replicons cannot be produced following initial cell entry in the absence of the missing nucleic acid. Replicons can lack this nucleic acid as a result of any modification of the wildtype poliovirus nucleic acid including, but not limited to, deletions, insertions, and substitutions, including an insertion of a nucleic acid encoding the polypeptide. In some embodiments, poliovirus replicons lack a wild type poliovirus nucleic acid that encodes at least a portion of a protein that is required for encapsidation. Proteins necessary for replicon encapsidation include proteins that are part of the capsid structure. Examples of such proteins are those encoded by the VP1, VP2, VP3, and VP4 genes of the poliovirus P1 capsid precursor region, the Vpg protein, and those proteins that are necessary for proper processing of structural proteins of the capsid structure, such as the proteases responsible for cleaving the viral polyprotein. Thus, in some embodiments, the poliovirus vector lacks nucleic acid sequences encoding one or more of VP1, VP2, VP3, and VP4, genes of the poliovirus P1 capsid precursor region, the Vpg protein, and encodes a Brachyury protein or Brachyury polypeptide.

Replicons are typically introduced into a cell in an RNA form. Encapsidated replicons are able to enter cells via interaction of the capsid proteins with poliovirus receptor. Replicons are fully capable of RNA replication (amplification) upon introduction into cells and translation, in the correct reading frame, of the single polyprotein through which expression of the entire replicon genome occurs. Translation of replicon sequences may be transient, usually lasting only about 24-48 hours. High levels of replicon-encoded proteins can accumulate during the translation period. Encapsidated replicons are able to enter cells via interaction of the capsid proteins with the hPVR protein.

In some embodiments, replicons comprise RNA, including sequences encoding Brachyury protein, and are encapsidated. In some examples, the replicons have a deletion of the capsid (P1) gene and are derived from the RNA genome of poliovirus type 1, type 2, type 3 or combinations thereof. Further, a nucleic acid encoding a Brachyury protein or Brachyury polypeptide can be substituted for part or all of the capsid (P1) gene such that the portion of the capsid (P1) gene which remains, if any, is insufficient to support encapsidation in vivo. Generally, the term “P1 replicons” refers to replicons in which the entire nucleic acid encoding the P1 capsid precursor protein has been deleted or altered such that the proteins which are normally encoded by this nucleic acid are not expressed or are expressed in a non-functional form. The proteins that are normally encoded by the P1 capsid precursor region of the poliovirus genome include the proteins encoded by the VP1, VP2, VP3, and VP4 genes. P1 replicons, therefore, lack the VP1, VP2, VP3, and VP4 genes or comprise unexpressible or non-functional forms of the VP1, VP2, VP3, and VP4 genes. P1 replicons can include a nucleic acid encoding a Brachyury protein or Brachyury polypeptide substituted for the VP1, VP2, VP3, and VP4 genes.

In some embodiments, encapsidated replicons may be produced by introducing both a replicon and a complementing expression vector that provides the missing nucleic acid necessary for encapsidation in trans to a host cell. A “replicon encapsidation vector” refers to a non-poliovirus-based vector that comprises a nucleic acid required for replicon encapsidation and provides the required nucleic acid (or encoded protein) in trans. Replicon encapsidation vectors can be introduced into a host cell prior to, concurrently with, or subsequent to replicon introduction. Suitable methods for encapsidation are disclosed in U.S. Pat. No. 6,680,169, which is incorporated by reference herein. Methods which can be used to prepare encapsidated replicons have been described Porter D C et al., J. Virol. 67:3712-3719, 1993; Porter D C et al., 1995, J. Virol. 69:1548-1555, 1995; PCT Publication No. WO 96/25173; U.S. Pat. Nos. 5,614,413, 5,817,512; 6,063,384; and 6,680,169.

Nonencapsidated replicons can be delivered directly to target cells, for example by direct injection into, for example, muscle cells (see, for example, Acsadi G et al., Nature 352(6338):815-818, 1991; Wolff J A et al., Science 247:1465-1468, 1990), or by electroporation, transfection mediated by calcium phosphate, transfection mediated by DEAE-dextran, liposome-mediated transfection or receptor-mediated nucleic acid uptake (see for example Wu G et al., J. Biol. Chem. 263:14621-14624, 1988; Wilson J M et al., J. Biol. Chem. 267:963-967, 1992; and U.S. Pat. No. 5,166,320), or other methods of delivering naked nucleic acids to target cells.

Retroviral Vectors: Retroviral vectors, including lentiviral vectors encoding the polypeptide are provided and are of use in the methods disclosed herein. Retroviral vectors have been tested and found to be suitable delivery vehicles for the stable introduction of a variety of genes of interest into the genomic DNA of a broad range of target cells. Without being bound by theory, the ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell-surface receptor as compared to the native envelope protein) can also be used.

Generally, retroviruses contain three major coding domains, gag, pol, env, which code for essential virion proteins. Retroviral vectors are of use wherein gag, pol and/or env are absent or not functional. Retroviral vectors are disclosed, for example, in U.S. Published Patent Application No. 20060286634.

Thus retroviral vectors are provided which include, for example, retroviral transfer vectors comprising a nucleic acid encoding the polypeptide and retroviral packaging vectors comprising one or more packaging elements. In some embodiments, pseudotyped retroviral vectors are provided encoding a heterologous or functionally modified envelope protein for producing pseudotyped retrovirus.

There are many retroviruses and examples include: murine leukemia virus (MLV), lentivirus such as human immunodeficiency virus (HIV), equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). Other retroviruses suitable for use include, but are not limited to, Avian Leukosis Virus, Bovine Leukemia Virus, Mink-Cell Focus-Inducing Virus. The core sequence of the retroviral vectors can be derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods disclosed herein, includes, but is not limited to, lentivirus.

One lentivirus is a human immunodeficiency virus (HIV), for example, type 1 or 2 (i.e., HIV-1 or HIV-2). Other lentivirus vectors include sheep Visna/maedi virus, feline immunodeficiency virus (FIV), bovine lentivirus, simian immunodeficiency virus (SIV), an equine infectious anemia virus (EIAV), and a caprine arthritis-encephalitis virus (CAEV).

Lentiviruses share several structural virion proteins in common, including the envelope glycoproteins SU (gp120) and TM (gp41), which are encoded by the env gene; CA (p24), MA (p117) and NC (p7-11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, such as by mutation or deletion.

Without being bound by theory, the use of lentivirus-based gene transfer techniques generally relies on the in vitro production of recombinant lentiviral particles carrying a highly deleted viral genome in which a gene of interest, such as a nucleic acid encoding the polypeptide, is accommodated. In particular, the recombinant lentivirus are recovered through the in trans co-expression in a permissive cell line of (1) the packaging constructs, i.e., a vector expressing the Gag-Pol precursors together with Rev (alternatively expressed in trans); (2) a vector expressing an envelope receptor, generally of an heterologous nature; and (3) the transfer vector, consisting in the viral cDNA deprived of all open reading frames, but maintaining the sequences required for replication, incapsidation, and expression, in which the sequences to be expressed are inserted. In one embodiment the lentigen lentiviral vector described in Lu, X. et al. Journal of gene medicine 6:963-973, 2004 is used to express the polypeptide. Suitable lentiviral vectors are also disclosed, for example, in U.S. Published Patent Application No. 20100062524.

Retroviral packaging systems for generating producer cells and producer cell lines that produce retroviruses, and methods of making such packaging systems are known in the art. Generally, the retroviral packaging systems include at least two packaging vectors: a first packaging vector which includes a first nucleotide sequence comprising a gag, a pol, or gag and pol genes; and a second packaging vector which includes a second nucleotide sequence comprising a heterologous or functionally modified envelope gene. In some embodiments, the retroviral elements are derived from a lentivirus, such as HIV. These vectors can lack a functional tat gene and/or functional accessory genes (vif, vpr, vpu, vpx, nef). In other embodiments, the system further comprises a third packaging vector that comprises a nucleotide sequence comprising a rev gene. The packaging system can be provided in the form of a packaging cell that contains the first, second, and, optionally, third nucleotide sequences.

First generation lentiviral vector packaging systems provide separate packaging constructs for gag/pol and env, and typically employ a heterologous or functionally modified envelope protein for safety reasons. In second generation lentiviral vector systems, the accessory genes, vif, vpr, vpu and nef, are deleted or inactivated. Third generation lentiviral vector systems are those from which the tat gene has been deleted or otherwise inactivated (e.g., via mutation). Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., liver-specific promoter), or other factors relating to desired control over expression, as is understood in the art. For example, in some embodiments, an inducible promoter such as tet can be used to achieve controlled expression. The gene encoding rev can be provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

Typically, the packaging vectors are included in a packaging cell, and are introduced into the cell via transfection, transduction or infection. Methods for transfection, transduction or infection are well known by those of skill in the art. A retroviral vector of the present invention can be introduced into a packaging cell line, via transfection, transduction or infection, to generate a producer cell or cell line. The packaging vectors can be introduced into human cells or cell lines by standard methods including, for example, calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. 93:11400-11406, 1996, which describe packaging cells. Zufferey et al., Nature Biotechnology 15:871-875, 1997 disclose a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter can be used.

The packaging vectors can include additional changes to the packaging functions to enhance lentiviral protein expression and to enhance safety. For example, all of the HIV sequences upstream of gag can be removed. Also, sequences downstream of envelope can be removed. Moreover, steps can be taken to modify the vector to enhance the splicing and translation of the RNA.

A self-inactivating vector (SIN) can be used, which improves the biosafety of the vector by deletion of the HIV-1 long terminal repeat (LTR) as described, for example, by Zufferey et al., J. Virology 72(12):9873-9880, 1998. Inducible vectors can also be used, such as through a tet-inducible LTR.

When the non-yeast vector is for administration to a host (e.g., human), the non-yeast vector (e.g., poxvirus) preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

In addition to the nucleic acid encoding the polypeptide, the non-yeast vector also can comprise polynucleotide(s)/gene(s) encoding one or more immunostimulatory/regulatory molecules, granulocyte macrophage colony stimulating factor (GM-CSF), cytokines, or other molecules that can enhance an immune response (e.g., additional tumor-associated antigens, such as prostate specific antigen (PSA), carcinoembryonic antigen (CEA) or modified versions thereof such as CEA-6D, and mucin (MUC) and modified versions thereof). The nucleic acid encoding the polypeptide, as well as any other exogenous gene(s), preferably are inserted into a site or region (insertion region) in the vector (e.g., poxvirus) that does not affect virus viability of the resultant recombinant virus. Such regions can be readily identified by testing segments of virus DNA for regions that allow recombinant formation without seriously affecting virus viability of the recombinant virus.

The thymidine kinase (TK) gene is an insertion region that can readily be used and is present in many viruses. In particular, the TK gene has been found in all examined poxvirus genomes. Additional suitable insertion sites are described in International Patent Application Publication WO 2005/048957. For example, in fowlpox, insertion regions include, but are not limited to the BamHI J fragment, EcoRI-HindIII fragment, BamHI fragment, EcoRV-HindIII fragment, long unique sequence (LUS) insertion sites (e.g., FPV006/FPV007 and FPV254/FPV255), FP14 insertion site (FPV060/FPV061), and 43K insertion site (FPV107/FPV108). In vaccinia, insertion sites include, but are not limited to, 44/45, 49/50, and 124/125.

When the non-yeast vector is a recombinant fowlpox virus comprising a nucleic acid encoding the polypeptide and/or other exogenous gene(s) (e.g., encoding one or more immunostimulatory/regulatory molecules), the nucleic acid encoding the polypeptide can be inserted in one region (e.g., the FP14 region), and the exogenous gene(s) can be inserted in another region (e.g., the BamHI J region).

The non-yeast vector can include suitable promoters and regulatory elements, such as a transcriptional regulatory element or an enhancer. When the vector is a poxvirus vector, poxvirus promoters can be used, including but not limited to the vaccinia 7.5K promoter, vaccinia 30K promoter, vaccinia 40K promoter, vaccinia I3 promoter, synthetic early/late (sE/L) promoter, 7.5 promoter, HH promoter, 11K promoter, and Pi promoter. While the promoters typically will be constitutive promoters, inducible promoters also can be used in the inventive vectors. Such inducible systems allow regulation of gene expression.

A non-yeast cell comprising the polypeptide, nucleic acid encoding the polypeptide, or on-yeast vector also is provided herein. Suitable cells include prokaryotic and eukaryotic cells, e.g., mammalian cells, non-yeast fungi, and bacteria (such as *E. coli, Salmonella* (e.g., *S. typhimurium*), or *Listeria* (e.g., *L. monocytogenes*). The non-yeast cell can be in vitro, as is useful for research or for production of the polypeptide, or the non-yeast cell can be in vivo. The non-yeast cell can be a polypeptide-pulsed antigen presenting cell. Suitable antigen presenting cells include, but are not limited to, dendritic cells, B lymphocytes, monocytes, macrophages, and the like.

In one embodiment, the non-yeast cell is dendritic cell. Dendritic cells of different maturation stages can be isolated based on the cell surface expression markers. For example, mature dendritic cells are less able to capture new proteins for presentation but are much better at stimulating resting T cells to grow and differentiate. Thus, mature dendritic cells can be of importance. Mature dendritic cells can be identified by their change in morphology and by the presence of various markers. Such markers include, but are not limited to, cell surface markers such as B7.2, CD40, CD11, and MHC class II. Alternatively, maturation can be identified by observing or measuring the production of pro-inflammatory cytokines.

Dendritic cells can be collected and analyzed using typical cytofluorography and cell sorting techniques and devices, such as a fluorescence-activated cell sorter (FACS). Antibodies specific to cell surface antigens of different stages of dendritic cell maturation are commercially available.

Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features.

Transformation of a host cell with recombinant DNA can be carried out by conventional techniques as are well known to those skilled in the art. Where the host is prokaryotic, such as, but not limited to, E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the non-yeast host cell if desired, or by electroporation.

When the cell is a eukaryote, such methods of transfection of DNA as calcium phosphate coprecipitates, conventional mechanical procedures such as microinjection, electroporation, insertion of a plasmid encased in liposomes, or infection with virus vectors can be used. Eukaryotic cells can also be co-transformed with polynucleotide sequences encoding the polypeptide, and a second foreign DNA molecule encoding a selectable phenotype, such as the herpes simplex thymidine kinase gene. Methods for using viral vectors to transform non-yeast eukaryotic cells are known, (see for example, Eukaryotic Viral Vectors, Cold Spring Harbor Laboratory, Gluzman ed., 1982).

The polypeptide, nucleic acid, non-yeast vector, or non-yeast cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

The polypeptide, nucleic acid, non-yeast vector, or non-yeast cell can be formulated as a composition (e.g., pharmaceutical composition) comprising the polypeptide, nucleic acid, non-yeast vector, or non-yeast cell and a carrier (e.g., a pharmaceutically or physiologically acceptable carrier). Furthermore, the polypeptide, nucleic acid, non-yeast vector, non-yeast cell, or composition of the invention can be used in the methods described herein alone or as part of a pharmaceutical formulation.

The composition (e.g., pharmaceutical composition) can comprise more than one polypeptide, nucleic acid, non-yeast vector, or non-yeast cell or composition of the invention. Alternatively, or in addition, the composition can comprise one or more other pharmaceutically active agents or drugs. Examples of such other pharmaceutically active agents or drugs that may be suitable for use in the pharmaceutical composition include anticancer agents (e.g., chemotherapeutic drugs), antibiotics, antiviral drugs, antifungal drugs, cyclophosphamide, and combinations thereof. Suitable anticancer agents include, without limitation, alkylating agents, nitrogen mustards, folate antagonists, purine antagonists, pyrimidine antagonists, spindle poisons, topoisomerase inhibitors, apoptosis inducing agents, angiogenesis inhibitors, podophyllotoxins, nitrosoureas, cisplatin, carboplatin, interferon, asparginase, tamoxifen, leuprolide, flutamide, megestrol, mitomycin, bleomycin, doxorubicin, irinotecan, taxol, geldanamycin (e.g., 17-AAG), and various anti-cancer polypeptides and antibodies known in the art.

The carrier can be any of those conventionally used and is limited only by physio-chemical considerations, such as solubility and lack of reactivity with the active compound(s) and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular polypeptide, nucleic acid, non-yeast vector, non-yeast cell, or composition thereof of the invention and other active agents or drugs used, as well as by the particular method used to administer the polypeptide, nucleic acid, non-yeast vector, non-yeast cell, or composition thereof.

The composition additionally or alternatively can comprise one or more immunostimulatory/regulatory molecules. Any suitable immunostimulatory/regulatory molecule can be used, such as interleukin (IL)-2, IL-4, IL-6, IL-12, interferon (IFN)-γ, tumor necrosis factor (TNF)-α, B7.1, B7.2, ICAM-1, LFA-3, CD70, RANTES, G-CSF, OX-40L, 41 BBL, anti-CTLA-4, and combinations thereof. Preferably, the composition comprises a combination of B7.1, ICAM-1, and LFA-3 (also referred to as TRICOM). The one or more immunostimulatory/regulatory molecules can be administered in the form of vector (e.g., a recombinant viral vector, such as a poxvirus vector) comprising a nucleic acid encoding one or more immunostimulatory/regulatory molecules. For example, the one or more immunostimulatory/regulatory molecules (e.g., IL-12) can be administered in the form of a DNA plasmid with or without chitosan. Alternatively, the one or more immunostimulatory/regulatory molecules can be administered as a protein (e.g., recombinant protein), such as a protein (e.g., recombinant IL-12) admixed with chitosan.

Brachyury protein is expressed in numerous human cancers, such as cancer of the small intestine, stomach, kidney bladder, uterus, ovary, testes, lung, colon, prostate, bronchial tube, chronic lymphocytic leukemia (CLL), other B cell-based malignancies and breast cancer, such as infiltrating ductal carcinomas of the breast. The administration of the polypeptide can be used to treat or prevent these cancers. In specific non-limiting examples, the breast cancer is an estrogen receptor negative and progesterone receptor negative breast cancer. In additional non-limiting examples, the cancer is any cancer that is radiation resistant and/or chemotherapy resistant. The cancer can express Brachyury or have the potential to express Brachyury.

The administration of the polypeptide, nucleic acid, non-yeast vector, or non-yeast cell can be used to induce $CD4^+$ Brachyury-specific T cells and/or $CD8^+$ T cells. Thus, methods are provided for inducing $CD4^+$ Brachyury-specific T cells and/or CD8+ T cells, which include the use of the polypeptide, nucleic acid, non-yeast vector, or non-yeast cell (e.g., dendritic cell) to induce the production of $CD4^+$ Brachyury specific T cells.

The invention also provides methods for treating a subject having cancer, such as, but not limited to, a cancer of the small intestine, stomach, kidney bladder, uterus, ovary, testes, lung, colon, prostate, bronchial tube, chronic lymphocytic leukemia (CLL), other B cell-based malignancies, or breast cancer, such as an infiltrating ductal carcinoma or estrogen receptor negative and progesterone receptor negative breast cancers. Any of these cancers can be chemotherapy resistant and/or radiation resistant. The cancer can express Brachyury or have the potential to express Brachyury. In specific non-limiting examples, the cancer is high grade prostatic intraepithelial neoplasia, familial adenomatous polyposis, or atypia of the breast. Methods are also disclosed for preventing these cancers.

These methods include inducing $CD4^+$ Brachyury-specific T cells. The methods can also include inducing $CD8^+$ Brachyury-specific T cells. The polypeptide, nucleic acid, non-yeast vector, and non-yeast cell can be administered to the subject either alone or in conjunction with a second agent, such as radiation therapy and/or chemotherapy.

In additional embodiments, methods are provided for inhibiting the growth of a cancer cell in a subject. These methods include contacting a dendritic cell with the polypeptide or a host cell expressing the polypeptide, thereby preparing a specific antigen presenting cell. These methods also include administering the antigen presenting cell to the subject, thereby inducing an immune response and inhibiting the growth of the cancer cell.

The methods can include selecting a subject in need of treatment, such as a subject with a cancer that expresses Brachyury or a cancer with the potential to express Brachyury. In several examples, the methods include selecting a subject with a cancer of the small intestine, stomach, kidney, bladder, uterus, ovaries, testes lung, colon, prostate, tumor of B cell origin (such as chronic lymphocytic leukemia (CLL), a B cell lymphoma, Burkitt's lymphoma or a Hodgkin's lymphoma) or breast cancer wherein the cancer expresses Brachyury or has the potential to express Brachyury. In some non-limiting examples, examples, the cancer is radiation resistant and/or chemotherapy resistant. In additional non-limiting examples, the subject has breast cancer, such as a ductal carcinoma, for example an infiltrating ductal carcinoma or an estrogen receptor negative and progesterone receptor negative breast cancer. In further examples, the subject has high-grade prostatic intraepithelial neoplasia, familial adenomatous polyposis, or atypia of the breast.

In exemplary applications, compositions are administered to a subject in an amount sufficient to raise an immune response to Brachyury-expressing cells, such as a $CD4^+$ T cell response. A Brachyury specific $CD8^+$ T cell response can also be induced using the methods disclosed herein. Administration induces a sufficient immune response to slow the proliferation of Brachyury-expressing cells, or to inhibit their growth, or to reduce a sign or a symptom of the cancer, or to prevent a cancer. Amounts effective for this use will depend upon the severity of the disease, the general state of the patient's health, and the robustness of the patient's immune system. In one example, a therapeutically effective amount of the composition is that which provides either subjective relief of a symptom(s) or an objectively identifiable improvement as noted by the clinician or other qualified observer.

The composition can be administered by any means known to one of skill in the art. Thus, the composition can be administered either locally or systemically, such as by intramuscular, subcutaneous, intraperitoneal or intravenous injection, but even oral, nasal, transdermal or anal administration is contemplated. In one embodiment, administration is by subcutaneous or intramuscular injection.

The polypeptide can be provided as an implant, an oily injection, in a liposome, or as a particulate system. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release. Adjuvants can also be used in combination with the protein, including, for example, chitosan, aluminum salts, an immunostimulatory oligodeoxynucleotide, liposomes and/or one or more cytokines. The polypeptide can be administered in a liposome.

In one specific, non-limiting example, the polypeptide is administered in a manner to direct the immune response to a cellular response (that is, a Brachyury specific $CD4^+$ response and/or $CD8^+$ response), rather than a humoral (antibody) response. The polypeptide can induce both a Brachyury specific $CD4^+$ T cell response and a Brachyury specific $CD8^+$ T cell response. Methods for measuring a $CD4^+$ and $CD8^+$ T cell response are known in the art, and include biological assays, ELISPOT assays, and fluorescence activated cell sorting. An exemplary assay for measuring Brachyury specific $CD4^+$ T cells is disclosed in the examples below.

In one specific, non-limiting example, a pharmaceutical composition for intravenous administration would include about 0.1 μg to 10 mg of the polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as Remington's Pharmaceutical Sciences, 19th Ed., Mack Publishing Company, Easton, Pa., 1995.

Optionally, one or more immunostimulatory molecules, such as IL-2, IL-6, IL-12, LFA (for example, LFA-1, LFA-2 and/or LFA-3), CD72, RANTES, G-CSF, GM-CSF, TNF-α, IFN-γ, ICAM-1, B7-1, B7-2, other B7 related molecules, OX-40L and/or or 41 BBL, or combinations of these molecules, can be used as biological adjuvants (see, for example, Salgaller et al., 1998, J. Surg. Oncol. 68(2):122-38; Lotze et al., 2000, Cancer J Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B7-2, OX-40L, 41 BBL and/or ICAM-1 are administered. IL-15 or an IL-15/IL-15 receptor complex can be administered.

A number of means for inducing cellular responses, both in vitro and in vivo, are known. Lipids have been identified as agents capable of assisting in priming T cells in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic polypeptide or protein. The lipidated polypeptide can then be injected directly in a micellar form, incorporated in a liposome, or emulsified in an adjuvant. As another example, E. coli lipoproteins, such as tripalmitoyl-S-glycerylcysteinlyseryl-serine can be used to prime tumor specific T cells when covalently attached to an appropriate polypeptide or protein (see, Deres et al., Nature 342:561, 1989). Further, as the induction of neutralizing antibodies can also be primed with the same molecule conjugated to a protein which displays an appropriate epitope, two compositions can be combined to elicit both humoral and cell-mediated responses where that is deemed desirable.

In one embodiment, the polypeptide is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, J. Am. Oil. Chem. Soc. 54:110, 1977, and Hunter et al., J. Immunol 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, J. Immun. 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.).

The polypeptide, nucleic acid, non-yeast vector, non-yeast cell, or composition thereof can be administered to the host by any method. For example, the polypeptide or nucleic acid encoding the polypeptide (e.g., as a non-yeast vector) can be introduced into a cell (e.g., in a host) by any of various techniques, such as by contacting the cell with the polypeptide, the nucleic acid, or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

Suitable methods of administering polypeptides, nucleic acids, non-yeast vectors, non-yeast cells, and compositions to hosts (subjects) are known in the art. The host (subject) can be any suitable host, such as a mammal (e.g., a rodent, such as a mouse, rat, hamster, or guinea pig, rabbit, cat, dog, pig, goat, cow, horse, primate, or human).

For example, the polypeptide, nucleic acid, or non-yeast vector (e.g., recombinant poxvirus) can be administered to a host by exposure of tumor cells to the polypeptide, nucleic acid, or non-yeast vector ex vivo or by injection of the polypeptide, nucleic acid, or non-yeast vector into the host. The polypeptide, nucleic acid, non-yeast vector (e.g., recombinant poxvirus) or combination of non-yeast vectors, non-yeast cells, and compositions can be directly administered (e.g., locally administered) by direct injection into the cancerous lesion or tumor or by topical application (e.g., with a pharmaceutically acceptable carrier).

The polypeptide, nucleic acid, non-yeast vector, non-yeast cell, or composition thereof can be administered alone or in combination with adjuvants, incorporated into liposomes (as described in, e.g., U.S. Pat. Nos. 5,643,599, 5,464,630, 5,059,421, and 4,885,172), with cytokines, with biological response modifiers (e.g., interferon, interleukin-2 (IL-2), and colony-stimulating factors (CSF, GM-CSF, and G-CSF), or other reagents in the art that are known to enhance immune response.

Examples of suitable adjuvants include alum, aluminum salts, aluminum phosphate, aluminum hydroxide, aluminum silica, calcium phosphate, incomplete Freund's adjuvant, QS21, MLP-A, and RIBI DETOX™.

A particularly preferred adjuvant for use in the invention is the cytokine GM-CSF. GM-CSF has been shown to be an effective vaccine adjuvant because it enhances antigen processing and presentation by dendritic cells. Experimental and clinical studies suggest that recombinant GM-CSF can boost host immunity directed at a variety of immunogens.

GM-CSF can be administered using a viral vector (e.g., poxvirus vector) or as an isolated protein in a pharmaceutical formulation. GM-CSF can be administered to the host before, during, or after the initial administration of the polypeptide, nucleic acid, non-yeast vector, cell, or composition thereof to enhance the antigen-specific immune response in the host. For example, recombinant GM-CSF protein can be administered to the host on each day of vaccination with the polypeptide, nucleic acid, non-yeast vector, cell, or composition thereof and for each of the following 3 days (i.e. a total of 4 days). Any suitable dose of GM-CSF can be used. For instance, 50-500 µg (e.g., 100 µg, 200 µg, 300 µg, 400 µg, and ranges thereof) of recombinant GM-CSF can be administered per day. The GM-CSF can be administered by any suitable method (e.g., subcutaneously) and, preferably, is administered at or near the site of the vaccination of a host with the polypeptide, nucleic acid, non-yeast vector, cell, or composition thereof.

In one embodiment, the inventive polypeptide can be conjugated to helper peptides or to large carrier molecules to enhance the immunogenicity of the polypeptide. These molecules include, but are not limited to, influenza peptide, tetanus toxoid, tetanus toxoid CD4 epitope, Pseudomonas exotoxin A, poly-L-lysine, a lipid tail, endoplasmic reticulum (ER) signal sequence, and the like.

The inventive polypeptide also can be conjugated to an immunoglobulin molecule using art-accepted methods. The immunoglobulin molecule can be specific for a surface receptor present on tumor cells, but absent or in very low amounts on normal cells. The immunoglobulin also can be specific for a specific tissue (e.g., breast, ovarian, colon, or prostate tissue). Such a polypeptide-immunoglobulin conjugate allows for targeting of the peptide to a specific tissue and/or cell.

Any suitable dose of the polypeptide, nucleic acid, non-yeast vector, or cell or composition thereof can be administered to a host. The appropriate dose will vary depending upon such factors as the host's age, weight, height, sex, general medical condition, previous medical history, disease progression, and tumor burden and can be determined by a clinician. For example, the peptide can be administered in a dose of about 0.05 mg to about 10 mg (e.g., 0.1 mg, 0.5 mg, 1 mg, 2 mg, 3 mg, 4 mg, 5 mg, 6 mg, 7 mg, 8 mg, 9 mg, and ranges thereof) per vaccination of the host (e.g., mammal, such as a human), and preferably about 0.1 mg to about 5 mg per vaccination. Several doses (e.g., 1, 2, 3, 4, 5, 6, or more)

can be provided (e.g., over a period of weeks or months). In one embodiment a dose is provided every month for 3 months.

When the non-yeast vector is a viral vector, a suitable dose can include about $1\times10^5$ to about $1\times10^{12}$ (e.g., $1\times10^6$, $1\times10^7$, $1\times10^8$, $1\times10^9$, $1\times10^{10}$, $1\times10^{11}$, and ranges thereof) plaque forming units (pfus), although a lower or higher dose can be administered to a host. For example, about $2\times10^8$ pfus can be administered (e.g., in a volume of about 0.5 mL).

The inventive cells (e.g., cytotoxic T cells) can be administered to a host in a dose of between about $1\times10^5$ and $2\times10^{11}$ (e.g., $1\times10^6$, $1\times10^7$, $1\times10^8$, $1\times10^9$, $1\times10^{10}$, and ranges thereof) cells per infusion. The cells can be administered in, for example, one to three (e.g., two) infusions. In addition to the administration of the cells, the host can be administered a biological response modifier, such as interleukin 2 (IL-2). When the cells to be administered are cytotoxic T cells, the administration of the cytotoxic T cells can be followed by the administration of the polypeptide, nucleic acid, non-yeast vector, or composition thereof in order to prime the cytotoxic T cells to further expand the T cell number in vivo.

When the cells to be administered are dendritic cells, the amount of dendritic cells administered to the subject will vary depending on the condition of the subject and should be determined via consideration of all appropriate factors by the practitioner. Preferably, about $1\times10^6$ to about $1\times10^{12}$ (e.g., about $1\times10^7$, about $1\times10^8$, about $1\times10^9$, about $1\times10^{10}$, or about $1\times10^{11}$ including ranges of any of the cell numbers described herein) dendritic cells are utilized for adult humans. These amounts will vary depending on the age, weight, size, condition, sex of the subject, the type of tumor to be treated, the route of administration, whether the treatment is regional or systemic, and other factors. Those skilled in the art should be readily able to derive appropriate dosages and schedules of administration to suit the specific circumstance and needs of the subject.

The invention includes a prime and boost protocol. In particular, the protocol includes an initial "prime" with a composition comprising one or more recombinant non-yeast vectors encoding the inventive polypeptide and optionally one or more immunostimulatory/regulatory molecules and/or other tumor-associated antigens (e.g., CEA, MUC), modified versions thereof, and immunogenic epitopes thereof, followed by one or preferably multiple "boosts" with a composition containing the inventive polypeptide or one or more non-yeast vectors encoding the inventive polypeptide and optionally one or more immunostimulatory/regulatory molecules and/or other tumor-associated antigens (e.g., CEA, MUC), modified versions thereof, and immunogenic epitopes thereof.

The initial priming vaccination can comprise one or more non-yeast vectors. In one embodiment, a single non-yeast vector (e.g., poxvirus vector) is used for delivery of the inventive polypeptide and optionally one or more immunostimulatory/regulatory molecules and/or other tumor-associated antigens (e.g., CEA, MUC), modified versions thereof, and immunogenic epitopes thereof. In another embodiment, two or more non-yeast vectors (e.g., poxvirus vectors) comprise the priming vaccination, which are administered simultaneously in a single injection.

The boosting vaccinations also can comprise one or more non-yeast vectors (e.g., poxvirus vectors). In one embodiment, a single non-yeast vector is used for delivery of the inventive polypeptide and optionally one or more immunostimulatory/regulatory molecules and/or other tumor-associated antigens (e.g., CEA, MUC), modified versions thereof, and immunogenic epitopes thereof of the boosting vaccination. In another embodiment, two or more non-yeast vectors comprise the boosting vaccination, which are administered simultaneously in a single injection.

Different non-yeast vectors (e.g., poxvirus vectors) can be used to provide a heterologous prime/boost protocol using vectors carrying different sets of therapeutic molecules for inoculations at different time intervals. For example, in one heterologous prime/boost combination, a first orthopox vector composition is used to prime, and a second avipox vector composition is used to boost.

The schedule for administration of the non-yeast vectors (e.g., poxvirus vectors) typically involves repeated administration of the boosting vector. The boosting vector can be administered 1-3 times (e.g., 1, 2, or 3 times) at any suitable time period (e.g., every 2-4 weeks) for any suitable length of time (e.g., 6-12 weeks for a total of at least 5-15 boosting vaccinations). For example, the primary vaccination can comprise a recombinant vaccinia or MVA vector followed by multiple booster vaccinations with an avipox vector. In a particular embodiment, the host receives one vaccination with the priming vector, followed every 2 weeks thereafter with the boosting vector for 6 boosts, followed by every 4 weeks thereafter with the boosting vector, and continuing with the boosting vector for a period of time dependent on disease progression.

The invention further provides a kit that has at least a first recombinant non-yeast vector (e.g., poxvirus vector) that has incorporated into its genome or portion thereof a nucleic acid encoding the inventive polypeptide in a pharmaceutically acceptable carrier. The first recombinant non-yeast vector (e.g., poxvirus vectors) also can comprise one or more nucleic acids encoding one or more immunostimulatory/regulatory molecules and/or other tumor-associated antigens (e.g., CEA, MUC), modified versions thereof, and immunogenic epitopes thereof. In addition to the first recombinant non-yeast vector, the kit can have a second recombinant non-yeast vector that comprises one or more nucleic acids encoding the one or more immunostimulatory/regulatory molecules and/or other tumor-associated antigens (e.g., CEA, MUC), modified versions thereof, and immunogenic epitopes thereof in a pharmaceutically acceptable carrier. The kit further provides containers, injection needles, and instructions on how to use the kit. In another embodiment, the kit further provides an adjuvant such as GM-CSF and/or instructions for use of a commercially available adjuvant with the kit components.

The polypeptide, nucleic acid, non-yeast vector, non-yeast cell, or composition thereof can be administered to a host by various routes including, but not limited to, subcutaneous, intramuscular, intradermal, intraperitoneal, intravenous, and intratumoral. When multiple administrations are given, the administrations can be at one or more sites in a host.

Administration of the polypeptide, nucleic acid, non-yeast vector, non-yeast cell, or composition thereof can be "prophylactic" or "therapeutic." When provided prophylactically, the polypeptide, nucleic acid, non-yeast vector, non-yeast cell, or composition thereof is provided in advance of tumor formation to allow the host's immune system to fight against a tumor that the host is susceptible of developing. For example, hosts with hereditary cancer susceptibility are a preferred group of patients treated with such prophylactic immunization. The prophylactic administration of the polypeptide, nucleic acid, non-yeast vector, non-yeast cell, or composition thereof prevents, ameliorates, or delays cancer. When provided therapeutically, the polypeptide, nucleic acid, non-yeast vector, non-yeast cell, or composition thereof is provided at or after the diagnosis of cancer.

When the host has already been diagnosed with cancer or metastatic cancer, the polypeptide, nucleic acid, non-yeast vector, non-yeast cell, or composition thereof can be administered in conjunction with other therapeutic treatments such as chemotherapy or radiation.

In a preferred embodiment, the administration of the polypeptide, nucleic acid, non-yeast vector, non-yeast cell, or composition thereof to a host results in a host cell expressing the inventive polypeptide and optionally one or more immunostimulatory/regulatory molecules and/or other tumor-associated antigens (e.g., CEA, MUC), modified versions thereof, and immunogenic epitopes thereof that were co-administered. The inventive polypeptide can be expressed at the cell surface of the infected host cell. The one or more immunostimulatory/regulatory molecules and/or other tumor-associated antigens (e.g., CEA, MUC), modified versions thereof, and immunogenic epitopes thereof can be expressed at the cell surface or may be actively secreted by the host cell. The expression of both the epitope and the immunostimulatory/regulatory molecule provides the necessary MHC restricted peptide to specific T cells and the appropriate signal to the T cells to aid in antigen recognition and proliferation or clonal expansion of antigen specific T cells. The overall result is an upregulation of the immune system. Preferably, the upregulation of the immune response is an increase in antigen specific T-helper lymphocytes and/or cytotoxic lymphocytes, which are able to kill or inhibit the growth of a cancer (e.g., breast cancer, ovarian cancer, colon cancer, lung cancer, thyroid cancer, gastric cancer, head and neck cancer, or prostate cancer) cell.

There are a variety of suitable formulations of the pharmaceutical composition for the inventive methods. The following formulations for parenteral, subcutaneous, intravenous, intramuscular, and intraperitoneal administration are exemplary and are in no way limiting. One skilled in the art will appreciate that these routes of administering the peptide, nucleic acid, non-yeast vector, non-yeast cell, or composition of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The peptide, nucleic acid, vector, cell, or composition thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, and synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The following examples further illustrate the invention but, of course, should not be construed as in any way limiting its scope.

EXAMPLE 1

This example provides materials and methods for the experiments described in Example 2.

Viral Construction

Ad5 [E1-, E2b-]-Brachyury, Ad5 [E1-, E2b-]-CEA and Ad5 [E1-, E2b-]-MUC1 were constructed and produced as previously described in Gabitzsch et al., (Cancer Immunol Immunother. 2010; 59: 1131-1135) and Amalfitano et al. (J Virol. 1998; 72: 926-933). Briefly, the transgenes were sub-cloned into the E1 region of the Ad5 [E1-, E2b-] vector using a homologous recombination-based approach. The replication deficient virus was propagated in the E.C7 packaging cell line, CsCl2 purified, and titered as previously described in Amalfitano et al., supra. Viral infectious titer was determined as plaque-forming units (PFUs) on an E.C7 cell monolayer. The VP concentration was determined by sodium dodecyl sulfate (SDS) disruption and spectrophotometry at 260 nm and 280 nm (ViraQuest, North Liberty, Iowa). The CEA transgene also contains a modified CEA containing the highly immunogenic epitope CAP1-6D (see Salazar et al., Int J Cancer. 2000; 85: 829-838; and Zaremba et al., Cancer Res. 1997; 57: 4570-4577).

The sequence encoding for the human Brachyury protein (NM 003181.3) was modified by introducing the enhancer T-cell HLA-A2 epitope (WLLPGTSTV; SEQ ID NO: 4) (see Tucker et al., Cancer Immunol Immunother. 2014; 63: 1307-1317) and removal of a 25 amino acid fragment involved in DNA binding. The resulting construct was subsequently subcloned into the Ad5 vector to generate the Ad5 [E1-, E2b-]Brachyury construct.

The MUC1 molecule consists of two regions: the N-terminus (MUC1-N), which is the large extracellular domain of MUC1, and the C-terminus (MUC1-C), which has three regions: a small extracellular domain, a single transmembrane domain, and a cytoplasmic tail (see Lan et al., J Biol Chem. 1990; 265: 15294-15299). The cytoplasmic tail contains sites for interaction with signaling proteins and has been shown to act as an oncogene and a driver of cancer motility, invasiveness and metastasis (see Wei et al., Cancer Res. 2007; 67: 1853-1858; and Li et al., J Biol Chem. 2001; 276: 35239-35242).

For construction of the Ad5 [E1-, E2b-]-MUC1, the entire MUC1 transgene, including eight agonist epitopes previously described (see Tsang et al., Clin Cancer Res. 2004; 10: 2139-2149; and Jochems et al., Cancer Immunol Immunother. 2014; 63: 161-174), was subcloned into the Ad5 vector. The agonist epitopes included in the Ad5 [E1-, E2b-]-MUC1 vector bind to HLA-A2 (epitope P93L in the N-terminus, V1A and V2A in the VNTR region, and C1A, C2A and C3A in the C-terminus), HLA-A3 (epitope C5A), and HLA-A24 (epitope C6A in the C-terminus). The Tri-Ad5 vaccine was produced by combining of $10^{10}$ VP of Ad5 [E1-, E2b-]-Brachyury, Ad5 [E1-, E2b-]-CEA and Ad5 [E1-, E2b-]-MUC1 at a ratio of 1:1:1 ($3\times10^{10}$ VP total).

Generation of Human DCs from PBMCs

Dendritic cells (DCs) were generated from the peripheral blood mononuclear cells (PBMCs) of a prostate cancer patient (HLA-A2$^+$ and -A24$^+$) enrolled in a clinical trial employing a PSA-TRICOM vaccine in combination with ipilimumab (see Madan et al., Lancet Oncol. 2012; 13: 501-508), using the method previously described (see Cereda et al., Vaccine. 2011; 29: 4992-4999). Using PBMCs from this patient post-vaccination, individual T-cell lines specific for CEA, MUC1, and Brachyury could be established. An Institutional Review Board of the National Institutes of Health (NIH) Clinical Center approved the procedures, and informed consent was obtained in accordance with the Declaration of Helsinki. Briefly, PBMCs were isolated using lymphocyte separation medium gradient (ICN Biochemicals, Aurora, Va.), resuspended in AIM-V medium (Invitrogen, Carlsbad, Calif.) ($2\times10^7$ cells) and allowed to adhere in a 6-well plate for 2 hours. Adherent cells were cultured for 5 days in AIM-V medium containing 100 ng/ml of recombinant human (rh) GM-CSF and 20 ng/ml of rhIL-4. The culture medium was replenished every 3 days.

Infection of Human DCs with Adenovirus Vectors

Dendritic cells ($2\times10^5$) in 1 ml of AIM-V medium were infected with adenovirus vectors (Ad5 [E1-, E2b-]-CEA, Ad5 [E1-, E2b-]-MUC1, Ad5 [E1-, E2b-]-Brachyury, and Ad5 [E1-, E2b-]-null at indicated multiplicity of infection (MOI of 10,000 or 20,000) for 1 hour in 6-well plates. AIM-V medium (4 ml) was then added to each well and incubated for an additional 2 days. To analyze the efficacy of transgene expression, DCs were harvested and analyzed using flow cytometry and Western blot. For phenotypic analysis, DCs were stained for the expression of CD80, CD83, CD86, CEA, and HLA-DR using BV421-conjugated anti-CD80, PerCP Cy5.5-conjugated anti-CD83, APC-Cy7-conjugated anti-HLA-DR, PE-conjugated anti-CD86, and FITC-conjugated anti-CEA. Antibodies for flow cytometry were purchased from BD Bioscience (San Jose, Calif.).

Generation of T-Cell Lines Using Adenovirus-Infected DCs

A modification of the method described by Tsang et al. (J Natl Cancer Inst. 1995; 87: 982-990) was used to generate CEA-, MUC1- and Brachyury-specific cytotoxic T lymphocytes (CTLs). Dendritic cells (1-$2\times10^5$/well in 1 ml of AIM-V) were infected with 20,000 MOI of Tri-Ad5, as described above. Infected DCs were used as APCs for stimulation of autologous nonadherent cells at an effector-APC ratio of 10:1. Cultures were incubated for 3 days at 37° C. in a humidified atmosphere containing 5% $CO_2$.

The cultures were then supplemented with rhIL-2 for 7 days; IL-2 containing medium was replenished every 3 days. The 10-day stimulation constituted one in vitro stimulation (IVS) cycle. Autologous vector-infected DCs were used as APCs for three IVS. Autologous peptide-pulsed B cells were used to restimulate antigen-specific CTLs after three IVS. T-cell lines were maintained in medium containing IL-7 and IL-15 (10 ng/ml; PeproTech, Rocky Hill, N.J.).

Cytotoxic Assay

A modification of the protocol described by Tsang et al. (Cancer Res. 2001; 61: 7568-7576) was used for CTL analysis. In brief, target cells were labeled with 50 µCi of $^{111}$In oxide (GE Health Care, Vienna, Va.) at 37° C. for 20 min and used at 3,000 cells/well in 96-well round-bottom culture plates. T cells were added at different ratios and incubated at 37° C. for 16 hours. Supernatants were harvested for gamma counting. Determinations were carried out in triplicate and SDs were calculated. Spontaneous release was determined by incubating target cells with medium alone and complete lysis was determined by incubating with 0.25% Triton X-100. Specific lysis was calculated with the use of the following formula: Lysis (%)=[observed release (CPM)−spontaneous release (CPM)]/[Complete release (CPM)−spontaneous release (CPM)]×100.

Tumor Cell Culture

Human colon carcinoma SW620 (HLA-A2$^+$, HLA-A24$^+$, Brachyury$^+$, MUC1$^+$, CEA$^+$) and pancreatic carcinoma ASPC-1 (HLA-A1$^+$, HLA-A26$^+$, MUC1$^+$) cell lines were obtained from American Type Culture Collection (Manassas, Va.). Cell cultures were free of mycoplasma and maintained in complete medium (RPMI-1640 supplemented with 10% FBS, 100 U/ml penicillin, 100 µg/ml streptomycin and 2 mM L-glutamine) (Mediatech, Herndon, Va.).

Detection of Cytokines

Supernatants of T cells stimulated for 24 hours with DCs infected with adenovirus vectors or peptide-pulsed DCs in IL-2-free medium were evaluated for secretion of IFN-γ using an ELISA kit (Invitrogen, Frederick, Md.). The antigen-specific T-cell lines used in this analysis have been reported previously: (a) an HLA-A2 CEA-specific CTL (Palena et al., Cytokine. 2003; 24: 128-142), (b) an HLA-A2 MUC1-specific CTL (Tsang et al., Clin Cancer Res. 2004; 10: 2139-2149), (c) an HLA-A24 MUC1-specific CTL (Jochems et al., Cancer Immunol Immunother. 2014; 63: 161-174), and (d) an HLA-A2 Brachyury-specific CTL (Tucker et al., Cancer Immunol Immunother. 2014; 63: 1307-1317).

Peptides

The following HLA-A2 and HLA-A24 binding peptides were used in this study: (a) the HLA-A2 binding CEA agonist peptide CAP1-6D (YLSGADLNL; SEQ ID NO: 5) (Zaremba et al., Cancer Res. 1997; 57: 4570-4577), (b) the HLA-A2 MUC1 agonist peptide P93L (ALWGQDVTSV; SEQ ID NO: 6) (Tsang et al., Clin Cancer Res. 2004; 10: 2139-2149), (c) the HLA-A24 binding MUC1 agonist peptide C6A (KYHPMSEYAL; SEQ ID NO: 7) (Jochems et al., Cancer Immunol Immunother. 2014; 63: 161-174), and (d) the HLA-A2 binding Brachyury agonist peptide (WLLPGT-STV; SEQ ID NO: 4) (Tucker et al., Cancer Immunol Immunother. 2014; 63: 1307-1317). All peptides were greater than 96% pure and manufactured by American Peptide Company, Inc. (Sunnyvale, Calif.).

Mice

Specific pathogen-free, female C57BL/6 mice (Jackson Laboratory, Bar Harbor, Me.) of ages 8-10 weeks were housed in animal facilities at the Infectious Disease Research Institute (IDRI) (Seattle, Wash., USA). All procedures were conducted according to Institutional Animal Care and Usage Committee (IACUC) approved protocols.

Vaccination and Splenocyte Preparation

Female C57BL/6 mice (n=5) were injected s.c. with $10^{10}$ VP of Ad5 [E1-, E2b-]-Brachyury or Ad5 [E1-, E2b-]-CEA or Ad5 [E1-, E2b-]-MUC1 or a combination of $10^{10}$ VP of all three viruses at a ratio of 1:1:1 (Tri-Ad5). Control mice were injected with $3\times10^{10}$ VP of Adeno-null (no transgene insert). Doses were administered in 25 µl of injection buffer (20 mM HEPES with 3% sucrose) and mice were vaccinated three times at 14-day intervals. Fourteen days after the final injection spleens and sera were collected. Sera were frozen at −20° C. Splenocyte suspensions were generated by gently crushing the spleens through a 70 µM nylon cell strainer (BD Falcon, San Jose, Calif.). Red cells were removed by the addition of red cell lysis buffer (Sigma-Aldrich, St. Louis, Mo.) and the splenocytes were washed twice and resuspended in R10 (RPMI 1640 supplemented with L-glutamine (2 mM), HEPES (20 mM) (Corning, Corning, N.Y.), penicillin 100 U/ml and streptomycin 100 µg/ml (Hyclone, GE Healthcare Life Sciences, Logan, Utah), and 10% fetal bovine serum (Hyclone). Splenocytes were assayed for cytokine production by ELISPOT and flow cytometry.

ELISPOT Assay

Brachyury-, CEA- and MUC1-specific IFN-γ- or IL-2-secreting T cells were determined by ELISPOT assay from freshly isolated mouse splenocytes, as described above. The ELISPOT assay was performed according to the manufacturer's specifications (Affymetrix Bioscience, San Diego, Calif.). Briefly, $2\times10^5$ splenocytes were stimulated with 0.2 µg/well of overlapping 15-mer peptides in a single pool derived from Brachyury or CEA (JPT Peptide Technologies, Berlin, Germany) or MUC1. Cells were stimulated with Concanavalin A (Con A) at a concentration of 0.0625 µg/per well as a positive control and overlapping 15-mer complete peptides pools derived from SIV-Nef and SIV-Vif (AIDS Research and Reference Reagent Program, Division of AIDS, National Institute of Allergy and Infectious Diseases (NIAID), National Institutes of Health (NIH)) were used as irrelevant peptide controls. The numbers of SFCs were determined using an Immunospot ELISpot plate reader (Cellular Technology, Shaker Heights, Ohio) and results were reported as the number of SFCs per $10^6$ splenocytes.

Intracellular Cytokine Stimulation

Splenocytes were prepared as indicated for above. Stimulation assays were performed using $1\times10^6$ live splenocytes per well in 96-well U-bottom plates. Pools of overlapping peptides spanning the entire coding sequences of Brachyury, CEA and MUC1 were synthesized as 15-mers with 11-amino acid overlaps (JPT GmbH) and lyophilized peptide pools were dissolved in Dimethyl sulfoxide (DMSO). Similarly constructed peptide pools corresponding to SIV-Vif and SIV-Nef served as off-target controls. Splenocytes in R10 media (RPMI 1640, 10% fetal bovine serum, and antibiotics) were stimulated by the addition of peptide pools at 2 µg/mL/peptide for 6 h at 37° C. and 5% $CO_2$, with protein transport inhibitor (GolgiStop, BD) added 2 h into the incubation. Stimulated splenocytes were then stained for lymphocyte surface markers CD8α and CD4, fixed, penneabilized, and then stained for the intracellular accumulation of IFN-γ and TNFα. Antibodies against mouse CD8α (clone 53-6.7), CD4 (clone RM4-5), IFN-γ (clone XMG1.2), and TNFα (clone MP6-XT22) were purchased from BD and staining was performed in the presence of anti-CD16/CD32 (clone 2.4G2). Flow cytometry was performed using an Accuri C6 Flow Cytometer (BD) and analyzed in BD Accuri C6 Software.

ELISA to Detect Antibodies Against CEA

ELISA plates (Maxisorp; Nunc, Rochester, N.Y.) were coated with 100 ng of human CEA (Sigma-Aldrich) in 0.05M carbonate-bicarbonate buffer pH 9.6 and incubated overnight at room temperature. Plates were washed three times with phosphate buffered saline containing 1% Tween-20 (PBS-T) and then blocked with PBS containing 1% BSA for 60 min at room temperature. After an additional three washes, sera diluted 1/50 in PBS-T were added to the wells and the plates were incubated for 1 hour at room temperature. Peroxidase labeled goat anti-mouse immunoglobulin (Ig) G (γ-chain specific) (Sigma-Aldrich) antibody at a 1:5000 dilution was added to the wells after washings and plates were incubated for 1 hour. Plates were washed three times and 1,2-phenylene-diamine substrate solution (Thermo-Fisher, Scientific, Waltham, Mass.) was added to each well. The reaction was stopped by adding 10% phosphoric acid. Absorbance was measured at 492 nm on a SpectraMax 190 ELISA reader (Molecular Devices, Sunnyvale, Calif.). The nanogram equivalents of IgG bound to CEA per well was obtained by reference to a standard curve generated using purified mouse IgG and developed at the same time as the CEA ELISA (Sigma-Aldrich) as previously described (see Gabitzsch et al., Vaccine. 2011; 29: 8101-8107). The results were analyzed and quantitated using SoftMax Pro 6.3 software (Molecular Devices).

Complement-Dependent Cytotoxicity Assay (CDC)

MC38-CEA2 tumor cells were cultured overnight at a density of $2\times10^4$ cells per well in 96-well tissue culture microplates. Pooled heat inactivated mouse sera were added at a 1:50 dilution and incubated at 37° C. for 1 hour. Rabbit serum was then added at a 1:50 dilution as a source of complement and cells were incubated an additional 2.5 hours at 37° C. Cell culture supernatants were assayed using Promega Cytotox 96 non-radioactive cytotoxicity assay (Promega, Madison, Wis.), according to the manufacturer's instructions. Percent lysis of MC38-CEA2 cells was calculated by the formula % lysis=(experimental−target spontaneous)/(target maximum−target spontaneous)×100%.

Tumor Immunotherapy

For in vivo tumor treatment studies, female C57BL/6 mice, 8-10 weeks old, were implanted with $10^6$ MC38-MUC1 cells s.c. in the left flank. Mice were treated three times at a 7-day interval with $10^{10}$ VP Adeno-MUC1 or Tri-Ad5. Control mice were injected with $3\times10^{10}$ VP of Adeno-null. Tumor growth was assessed by measuring two opposing dimensions (a, b) and the volume calculated as previously described (see Tomayko et al., Cancer Chemother Pharmacol. 1989; 24: 148-154) according to the formula V=(axb)²/2 where the shorter dimension was "a". Tumor studies were terminated when tumors reached 1500 m³ or became severely ulcerated.

EXAMPLE 2

This example describes the generation and characterization of vectors comprising the Brachyury deletion mutant polypeptide.

Recombinant Ad5 [E1-, E2b-]-CEA was generated and characterized as previously described (see Gabitzsch et al., Cancer Immunol Immunother. 2010; 59: 1131-1135). Recombinant Ad5 [E1-, E2b-]-MUC1 and Ad5 [E1-, E2b-]-Brachyury were generated as described in Example 1. Western blot analysis using an anti-Brachyury-specific monoclonal antibody (MAb 54-1) revealed Brachyury expression when human dendritic cells (DCs) were infected with Ad5 [E1-, E2b-]-Brachyury. An Ad5 [E1, E2b-] vector devoid of any transgene (Ad5 [E1-, E2b-]-null) was used as a negative control and SW620 human colon carcinoma cells that endogenously express Brachyury were used as a positive control.

An anti-MUC1-specific MAb was used to detect the expression of MUC1 in Ad5 [E1-, E2b-]-MUC1-infected human DCs. SW620 cells, which also express MUC1 endogenously, were used as a positive control. The difference in molecular weights seen in the human DCs versus the SW620 human carcinoma cells is most likely due to the differential glycosylation of the MUC1 protein.

It would appear that MUC1-C is being expressed in the human DCs predominantly as the unglycosylated 17 or 15 kDa form and not the 25-20 glycosylated species. Human DCs infected with Ad5 [E1-, E2b-]-CEA, Ad5 [E1-, E213-]-MUC1 and Ad5 [E1-, E2b-]-null were analyzed for evidence of DC maturation versus uninfected human DCs. There were no differences between the Ad5 [E1-, E2b-]-null and the recombinant Ad5 [E1-, E2b-] vectors expressing the TAAs in that each slightly upregulated surface CD80 and CD83 expression and strongly upregulated HLA-DR surface expression. It is thus apparent that any changes in DC maturation is due to the Ad5 vector alone and not any TAA transgene insertion.

The generation of Brachyury-, CEA-, and MUC1-specific human CD8+ T cells employing the corresponding peptide for each TAA were previously reported (see Palena et al., Clin Cancer Res. 2007; 13: 2471-2478; Tsang et al., Clin Cancer Res. 2004; 10: 2139-2149; Jochems et al., Cancer Immunol Immunother. 2014; 63: 161-174; Tucker et al., Cancer Immunol Irnmunother. 2014; 63: 1307-1317; Salazar et al., Int J Cancer. 2000; 85: 829-838; and Zaremba et al., Cancer Res. 1997; 57: 4570-4577).

As shown in Table 1, Ad5 [E1-, E2b-]-null did not activate any of the T cells to produce IFN-γ. Ad5 [E1-, E2b-]-Brachyury-infected DCs activated Brachyury-specific T cells and not CEA-specific T cells (as a negative control). This demonstrates that the Ad5 [E1-, E2b-]-Brachyury-infected DCs could process Brachyury in a manner that generates Brachyury-MHC Class I complexes capable of specific T-cell activation.

TABLE 1A

Infection of human dendritic cells with recombinant adenovirus vectors encoding CEA, MUC1 or Brachyury can activate antigen-specific T-cell lines

| Dendritic cells (DCs) infected with | Antigen-specific T-cell lines | | | |
|---|---|---|---|---|
| | CEA | MUC1 (HLA-A2) | MUC1 (HLA-A24) | Brachyury |
| Ad5 [E1-, E2b-]-null | <15.6 | <15.6 | <15.6 | <15.6 |
| Ad5 [E1-, E2b-]-Brachyury | <15.6 | — | — | 351.9 |
| Ad5 [E1-, E2b-]-MUC1 | <15.6 | 335.2 | 806.4 | |
| Ad5 [E1-, E2b-]-CEA | 350.0 | <15.6 | <15.6 | |
| Uninfected DCs | <15.6 | <15.6 | <15.6 | |
| | <15.6 | | | |
| T cells only | <15.6 | <15.6 | <15.6 | <15.6 |

Human DCs (6-day culture in IL-4 and granulocyte-macrophage colony-stimulating factor (GM-CSF) 2 × 10⁴ cells/well in 0.5 ml of AIM-V) were infected with indicated adenovirus vectors at 20,000 multiplicity of infection (MOI). After 48 hours, DCs were washed and used for stimulation of human antigen-specific T cells. Results are expressed in pg/ml of IFN-γ per 1 × 10⁵ T cells/ml. Numbers in bold indicate a significant enhancement of IFN-γ secretion compared to corresponding wells with uninfected DCs.
[— indicates that the assay was not performed.]

TABLE 1B

Infection of human dendritic cells with Tri-Ad5 vectors encoding transgenes can activate antigen-specific T cell lines to produce IFN-γ

| Dendritic cells (DCs) infected with | Antigen-specific T-cell lines | | | |
|---|---|---|---|---|
| | CEA (HLA-A2) | MUC1 (HLA-A2) | MUC1 (HLA-A24) | Brachyury (HLA-A2) |
| Tri-Ad5 | 480 | 236 | 763 | 496 |
| Ad5 [E1, E2b]-null | <15.6 | <15.6 | <15.6 | <15.6 |
| Uninfected DCs | <15.6 | <15.6 | <15.6 | <15.6 |
| T cells only | <15.6 | <15.6 | <15.6 | <15.6 |

Human DCs (6-day culture in IL-4 and GM-CSF) from an HLA-A2 and -A24 donor were infected with Tri-Ad5 vector at 2 × 10⁴/well (24-well plate) in 0.5 ml of AIM-V. Tri-Ad5 vectors were used at 20,000 MOI for 1 hour and then 1.5 ml of AIM-V were added to each well. Infected DCs were incubated for 48 hours and then washed and used for stimulation of human antigen-specific T cells. Results are expressed in pg of IFN-γ per 1 × 10⁵ T cells/ml. Numbers in bold indicate a significant enhancement of IFN-γ secretion compared to corresponding wells with uninfected DCs.

Similarly, Ad5 [E1-, E2b-]-CEA-infected DCs specifically activated CEA-specific T cells but not MUC1-specific T-cell lines. Both Class I HLA-A2 and -A24 MUC1-specific T-cell lines have been previously generated (see Jochems et al., Cancer Immunol Immunother. 2014; 63: 161-174) and the Ad5 [E1-, E2b-]-MUC1-infected DCs were capable of activating both of these T-cell lines but not the CEA-specific T-cell line (Table 1A). Human DCs were similarly infected with the Tri-Ad5 vector. As seen in Table 1B, T cells specific for CEA, MUC1, and Brachyury were each activated to induce similar levels of IFN-γ as seen with the use of the individual Ad-5 vectors.

Studies were then undertaken to determine whether simultaneous infection of human DCs with the CEA/MUC1/Brachyury mixture of Tri-Ad5 could generate T-cell lines specific for all three TAAs. As seen in Table 2, when the T cells were activated by incubation with autologous B cells pulsed with the corresponding peptide, and not a control peptide, specific T-cell activation was observed.

TABLE 2

Infection of human dendritic cells with Tri-Ad5 can generate antigen-specific T cells to Brachyury, MUC1 and CEA and produce IFN-γ when stimulated with autologous B cells pulsed with the corresponding peptides

| Antigen-specific T-cell lines | Peptides (10 μg/ml) | | | |
|---|---|---|---|---|
| | CEA | MUC1 (HLA-A2) | MUC1 (HLA-A24) | Brachyury |
| T-Brachyury | <15.6 | — | — | 243 |
| T-MUC1 (A2) | <15.6 | <15.6 | — | — |
| T-MUC1 (A24) | <15.6 | — | 206 | — |
| T-CEA | 211 | <15.6 | — | — |

Human dendritic cells (DCs) from a prostate cancer patient (6-day culture in IL-4 and granulocyte-macrophage colony-stimulating factor (GM-CSF) $2 \times 10^4$ cells/well in 0.5 ml of AIM-V) were infected with Tri-Ad5 at 20,000 MOI. After 48 hours, infected DCs were washed and used to generate specific cytotoxic T lymphocytes (CTLs) using autologous peripheral blood mononuclear cells (PBMCs) as effectors. Following 3 cycles of in vitro stimulations, autologous peptides-pulsed B cells were used as antigen-presenting cells. Results are expressed in pg/ml of IFN-γ.
[— indicates that the assay was not performed.]

For example, the Brachyury-specific T-cell line, generated by infecting human DCs with Tri-Ad5, was stimulated to produce IFN-γ when incubated with autologous DCs pulsed with Brachyury peptide, but was not activated with the same autologous DCs pulsed with a CEA peptide. Similar results were seen with CEA and MUC1 T-cell lines generated with Tri-Ad5-infected DCs. These results indicate the lack of so-called "antigenic competition" in the in vitro use of Tri-Ad5.

Whether Brachyury-, MUC1-, and CEA-specific human T cells generated using DCs infected with Tri-Ad5 could lyse human carcinoma cells that endogenously express these TAAs was then investigated. SW620 human colon carcinoma cells express all three TAAs and possess the HLA-A2 and -A24 Class I alleles. ASPC-1 human pancreatic carcinoma cells were used as a negative control since they express the three TAAs but in the context of HLA-A1 and -A26 molecules. The results (Table 3) demonstrated that Tri-Ad5-infected human DCs can generate T cells capable of lysing, in an MHC-restricted manner, human tumor cells that endogenously express Brachyury, CEA, and MUC 1.

TABLE 3

Infection of human DCs with Tri-Ad5 can generate Brachyury-, MUC1-, and CEA- specific CTLs that efficiently lyse tumor cells expressing all three antigens

| Antigen-specific T-cell lines | SW620 Brachyury+MUC1+CEA+ (HLA-A2+/A24+) | ASPC-1 Brachyury+MUC1+CEA+ (HLA-A2+/A26+) |
|---|---|---|
| T-Brachyury | 64.4 (3.6) | 8.3 (2.7) |
| T-MUC1 (P93L) | 28.5 (1.3) | 2.0 (1.6) |
| T-MUC1 (C6A) | 49.3 (3.3) | 5.0 (1.8) |
| T-CEA | 42.2 (3.7) | 4.3 (1.9) |

Human dendritic cells (DCs) were infected with Tri-Ad5 at 20,000 MOI. Infected DCs were used to generate specific cytotoxic T lymphocytes (CTLs) using autologous peripheral blood monoclonal cells (PBMCs). Autologous DCs were used as antigen-presenting cells for three in vitro stimulations (IVS). Autologous peptide-pulsed B cells pulsed were used to re-stimulate antigen-specific CTLs for two additional IVS. The effector-to-target ratio used was 30:1; CTLs were used at IVS 5. Results are expressed in % specific lysis (SD).

Studies were next undertaken to determine whether Ad5 [E1-, E2b-]-Brachyury, Ad5 [E1-, E2b-]-MUC1, and Ad5 [E1-, E2b-]-CEA could each generate TAA-specific T-cell responses in vivo, and whether the Tri-Ad5 mixture could generate comparable responses. C57B1/6 mice (n=5 per group) were injected subcutaneously (s.c.) three times at 2-week intervals with $10^{10}$ viral particles (VP) of Ad5 [E1-, E2b-]-CEA, Ad5 [E1-, E2b-]-MUC1, Ad5 [E1-, E2b-]-Brachyury, or Tri-Ad5 (1:1:1 mixture of $10^{10}$ VP each). An additional group of mice (n=5) received $3 \times 10^{10}$ VP of Ad5 [E1-, E2b-]-null (an empty vector control).

Two weeks after the final vaccination, splenocytes from vaccinated mice were stimulated with corresponding Brachyury, CEA, or MUC1 peptide pools and analyzed for IFN-γ and IL-2 secreting cells by the enzyme-linked immunospot (ELISPOT) assay. Mice vaccinated with singular constructs or with Tri-Ad5 responded to Brachyury, CEA, and MUC1 peptides, respectively, with significant increases in IFN-γ and IL-2 spot forming cells (SFCs) as compared to control mice (FIGS. 1A and B). There was no significant difference in the average number of IFN-γ SFCs in mice vaccinated with Ad5 [E1-, E2b-]-Brachyury or Ad5 [E1-, E2b-]-CEA individually as compared with the Tri-Ad5 vaccine. There was a significant decrease in IFN-γ SFCs in mice treated with the Tri-Ad5 vaccine as compared to Ad5 [E1-, E2b-]-MUC1 alone, although the MUC1-specific immune response induced by Tri-Ad5 remained significantly elevated over control mice (p<0.0001) (FIG. 2A). IL-2 responses were similar in mice treated with Tri-Ad5 versus single vaccine constructs; moreover, there was a significant increase (p=0.004) in CEA-specific IL-2 SFCs when mice were vaccinated with the Tri-Ad5 vaccine versus the Ad5 [E1-, E2b-]-CEA vaccine alone (FIG. 3B). Splenocytes from mice vaccinated with empty vector did not respond to Brachyury, CEA, or MUC1 peptide pools. In addition, there was no reactivity to control peptide pools (simian immunodeficiency virus (SIV)-Nef and SIV-Vif) in splenocytes from any of the vaccinated groups.

Taken together, these data indicate that combining Ad5 [E1-, E2b-]-Brachyury, Ad5 [E1-, E2b-]-CEA, and Ad5 [E1-, E2b-]-MUC1 in a Tri-Ad5 vaccine admixture has the effect of generating antigen-specific IFN-γ- and IL-2-producing cells similar to that achieved when using each vaccine alone.

Figure 2:
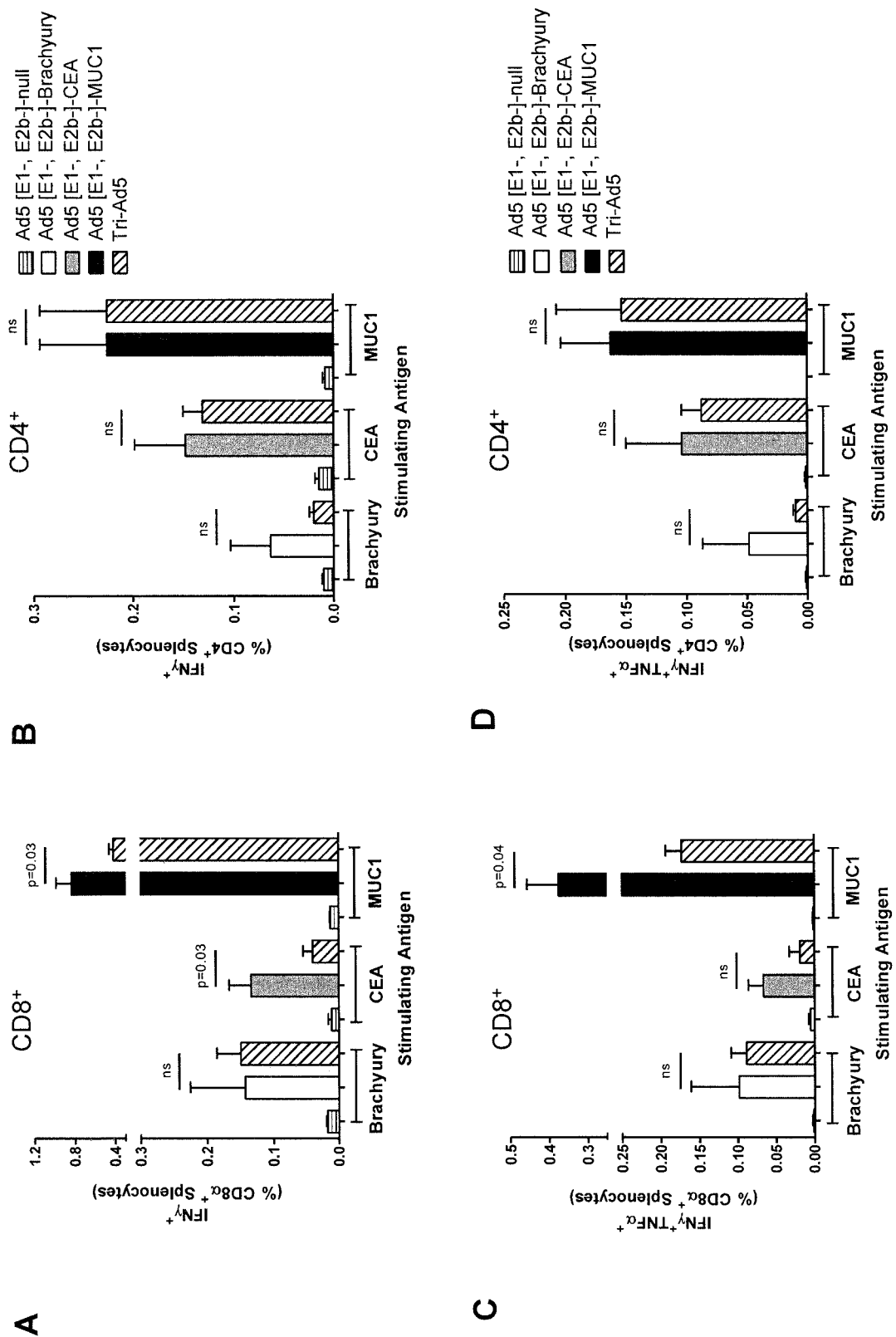

Intracellular accumulation of IFN-γ and TNF-α in CD8+ and CD4+ lymphocyte populations was also evaluated by flow cytometry using splenocytes from mice vaccinated with the adenovirus vectors and stimulated with overlapping pools of the respective synthetic peptides (FIG. 2). No significant differences were observed between the IFN-γ production observed with CD8+ splenic lymphocytes isolated from mice vaccinated with Ad5 [E1-, E2b-]-Brachyury compared with those isolated from mice vaccinated with Tri-Ad5 (FIG. 2A). Significant reductions between the CEA-specific and MUC1-specific IFN-γ accumulation in CD8+ splenocytes isolated from mice vaccinated with Tri-Ad5 as compared to single construct vaccinated mice were observed, although the relative number of SFCs remained significantly elevated over controls (p<0.0001) (FIG. 2A). However, no significant differences in IFN-γ accumulation between CD4+ splenocytes isolated from each single construct vaccinated mice or Tri-Ad5 vaccinated mice were found (FIG. 2B).

Peptide-stimulated splenocytes were also assessed by flow cytometry for the intracellular accumulation of both IFN-γ and TNF-α. Antigen-specific multifunctional CD8+ and CD4+ splenocytes in mice vaccinated with each single-antigen vector as well as with Tri-Ad5 were detected. When directly comparing the frequencies of dual-functional CD8+ and CD4+ splenocytes isolated from mice vaccinated with a single vector versus those from a mouse vaccinated with Tri-Ad5, very few differences were observed (FIGS. 2C and D). No significant differences were detected between the dual-functional CD8+ splenocytes isolated from mice vaccinated with Ad5 [E1-,E2b-]-Brachyury or Ad5 [E1-, E2b-]-CEA against the respective antigen as compared with those isolated from mice vaccinated with Tri-Ad5 (FIG. 2C). A significant reduction in dual-functional CD8+ splenocytes from mice vaccinated with Ad5 [E1-, E2b-]-MUC1 compared with Tri-Ad5 (p=0.04) was observed; this reduced frequency, however, was significantly elevated as compared to controls (p<0.001). No significant differences were found in the frequencies of multifunctional CD4+ splenocytes isolated from each single construct or Tri-Ad5 vaccinated mice (FIG. 2C).

To assess whether humoral responses were induced by Ad5 [E1-, E2b-]-CEA, Ad5 [E1-, E2b-]-MUC1, Ad5 [E1-, E2b-]-Brachyury, or Tri-Ad5 vaccines, antigen-specific quantitative enzyme-linked immunosorbent assays (ELISAs) were employed. Significant and comparable antibody responses were detected against CEA in sera from mice vaccinated with Ad5 [E1-,E2b-]-CEA or Tri-Ad5 (FIG. 3A). Antibodies against CEA were not detected in mice vaccinated with control vector (FIG. 3A), or mice vaccinated with Ad5 [E1-, E2b-]-Brachyury, or Ad5 [E1-, E2b-]-MUC1. Antigen-specific antibodies to Brachyury or MUC1 were not detected in sera of mice vaccinated with Ad5 [E1-, E2b-]-Brachyury, Ad5 [E1-, E2b-]-MUC1, or Tri-Ad5, respectively.

To determine the propensity of the CEA antibodies in the sera of Ad5 [E1-, E2b-]-CEA or Tri-Ad5 vaccinated mice to lyse tumor cells expressing CEA, a complement-dependent cytotoxicity (CDC) assay was utilized. Heat-inactivated sera from vaccinated mice were incubated with MC38-CEA2 tumor cells (murine CEA colon carcinoma cells transfected with human CEA), followed by rabbit sera as a source of complement. Lysis was determined by the release of lactate dehydrogenase (LDH) from MC38-CEA2 cells. There was significant lysis of MC38-CEA2 cells in sera from mice vaccinated with Tri-Ad5 or Ad5 [E1-, E2b-]-CEA, and this effect was similar between the two groups (FIG. 3B).

Studies were then undertaken to determine whether the Tri-Ad5 vaccine regimen was as effective as the use of a single recombinant adenovirus construct in eliciting an anti-tumor effect. C57BL/6 mice (n=7/group) were implanted s.c. with 1×10$^6$ MC38 cells expressing MUC1 (MC38-MUC1) in the left flank. Mice were vaccinated weekly with s.c. injections in the opposite flank using 10$^{10}$ VP of Ad5 [E1-, E2b-]-MUC1 or Tri-Ad5, respectively. A control group of mice received 3×10$^{10}$ VP of Ad5 [E1-, E2b-]-null (no transgene). Mice vaccinated with Ad5 [E1-, E2b-]-MUC1 or Tri-Ad5 had significantly smaller tumors than control mice on days 25 (p<0.01) and 29 (p<0.05) (FIG. 4). There was no significant difference (p>0.1) in anti-tumor effect for the groups of mice vaccinated with Ad5 [E1-, E2b-]-MUC1 or Tri-Ad5 at all time points.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A polypeptide comprising the amino acid sequence of SEQ ID NO: 3.

2. A non-yeast cell comprising (i) the polypeptide of claim 1.

3. A composition comprising:
   (a) (i) the polypeptide of claim 1, or (ii) a non-yeast cell comprising (i), and
   (b) a pharmaceutically acceptable carrier.

4. The composition of claim 3, further comprising an immunostimulatory/regulatory molecule.

5. The composition of claim 4, wherein the immunostimulatory/regulatory molecule is selected from the group consisting of interleukin (IL)-2, IL-4, IL-6, IL-12, interferon (IFN)-γ, tumor necrosis factor (TNF)-α, B7.1, B7.2, intracellular adhesion molecule (ICAM)-1, lymphocyte function-associated antigen (LFA)-3, cluster of differentiation 70 (CD70), regulated on activation, normal T cell expressed and secreted (RANTES), granulocyte-colony stimulating factor (G-CSF), OX40 ligand (OX-40L), 44 BBL ligand (41 BBL), anti-cytotoxic T-lymphocyte-associated protein 4 (anti-CTLA-4), and combinations thereof.

6. The composition of claim 5, wherein the immunostimulatory/regulatory molecule is selected from the group consisting of (i) a plasmid encoding IL-12 complexed with chitosan and (ii) recombinant IL-12 admixed with chitosan.

7. The composition of claim 3, further comprising a chemotherapeutic drug, antibiotic, antiviral drug, antifungal drug, cyclophosphamide, or a combination thereof.

8. The composition of claim 3, further comprising one or more adjuvants.

9. The composition of claim 8, wherein one or more adjuvants is selected from the group consisting of alum, aluminum salts, aluminum phosphate, aluminum hydroxide, aluminum silica, calcium phosphate, incomplete Freund's adjuvant, Quillaja saponaria fraction 21(QS21), monophosphoryl lipid A (MPL-A), and combinations thereof.

10. The composition of claim 3, further comprising granulocyte monocyte colony stimulating factor (GM-CSF).

11. The composition of claim 3, further comprising liposomes.

12. A method for inducing an immune response to Brachyury comprising administering to a subject an effective amount of (i) the polypeptide of claim 1, or (ii) non-yeast cell comprising of (i), or (iii) a composition comprising any one of (i)-(ii), thereby inducing the immune response, wherein the immune response comprises a Brachyury specific CD4+ T cell response.

13. The method of claim 12, wherein the immune response further comprises a Brachyury specific CD8$^+$ T cell response.

14. The method of claim 12, further comprising measuring the Brachyury specific CD4$^+$ T cell response.

15. The method of claim 12, comprising administering to the subject a liposome comprising the polypeptide.

16. The method of claim 12, further comprising administering to the subject a therapeutically effective amount of a second agent, wherein the second agent is a chemotherapeutic agent, radiation, a small molecule targeted therapeutic, hormonal therapies or checkpoint inhibitors.

17. The method of claim 16, wherein the checkpoint inhibitors are selected from the group consisting of anti-programmed cell death protein 1 (anti-PD-1), anti-programmed death-ligand 1 (anti-PD-L1), anti-cytotoxic T-lymphocyte-associated protein 4 (anti-CTLA-4), and combinations thereof.

18. The method of claim 16, wherein the second agent is an epithelial growth factor receptor inhibitor, a transforming growth factor (TGF)-β inhibitor, or a tyrosine kinase inhibitor.

* * * * *

SEQUENCE LISTING

```
<160> NUMBER OF SEQ ID NOS: 7

<210> SEQ ID NO 1
<211> LENGTH: 435
<212> TYPE: PRT
<213> ORGANISM: Artificial Sequence
<220> FEATURE:
<223> OTHER INFORMATION: Synthetic

<400> SEQUENCE: 1

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
```

```
            20                  25                  30
Glu Lys Gly Asp Pro Thr Glu Arg Glu Leu Arg Val Gly Leu Glu Glu
            35                  40                  45

Ser Glu Leu Trp Leu Arg Phe Lys Glu Leu Thr Asn Glu Met Ile Val
        50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Gln Tyr Pro Ser Leu Trp Ser
            340                 345                 350

Val Ser Asn Gly Ala Val Thr Pro Gly Ser Gln Ala Ala Val Ser
        355                 360                 365

Asn Gly Leu Gly Ala Gln Phe Phe Arg Gly Ser Pro Ala His Tyr Thr
    370                 375                 380

Pro Leu Thr His Pro Val Ser Ala Pro Ser Ser Ser Gly Ser Pro Leu
385                 390                 395                 400

Tyr Glu Gly Ala Ala Ala Thr Asp Ile Val Asp Ser Gln Tyr Asp
                405                 410                 415

Ala Ala Ala Gln Gly Arg Leu Ile Ala Ser Trp Thr Pro Val Ser Pro
            420                 425                 430

Pro Ser Met
    435
```

-continued

```
<210> SEQ ID NO 2
<211> LENGTH: 435
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (246)..(254)
<223> OTHER INFORMATION: agonist peptide

<400> SEQUENCE: 2

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Val Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Ser Gln Tyr Pro Ser Leu Trp Ser
```

```
            340                 345                 350
Val Ser Asn Gly Ala Val Thr Pro Gly Ser Gln Ala Ala Val Ser
            355                 360                 365
Asn Gly Leu Gly Ala Gln Phe Phe Arg Gly Ser Pro Ala His Tyr Thr
        370                 375                 380
Pro Leu Thr His Pro Val Ser Ala Pro Ser Ser Gly Ser Pro Leu
385                 390                 395                 400
Tyr Glu Gly Ala Ala Ala Thr Asp Ile Val Asp Ser Gln Tyr Asp
                405                 410                 415
Ala Ala Ala Gln Gly Arg Leu Ile Ala Ser Trp Thr Pro Val Ser Pro
                420                 425                 430
Pro Ser Met
        435

<210> SEQ ID NO 3
<211> LENGTH: 410
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (229)..(229)
<223> OTHER INFORMATION: wherein Xaa is Ser or Val

<400> SEQUENCE: 3

Met Ser Ser Pro Gly Thr Glu Ser Ala Gly Lys Ser Leu Gln Tyr Arg
1               5                   10                  15
Val Asp His Leu Leu Ser Ala Val Glu Asn Glu Leu Gln Ala Gly Ser
                20                  25                  30
Glu Lys Gly Asp Pro Thr Glu Arg Glu Leu Arg Val Gly Leu Glu Glu
            35                  40                  45
Ser Glu Leu Trp Leu Arg Phe Lys Glu Leu Thr Asn Glu Met Ile Val
        50                  55                  60
Thr Lys Asn Gly Arg Arg Met Phe Pro Val Leu Lys Val Asn Val Ser
65                  70                  75                  80
Gly Leu Asp Pro Asn Ala Met Tyr Ser Phe Leu Leu Asp Phe Val Ala
                85                  90                  95
Ala Asp Asn His Arg Trp Lys Tyr Val Asn Gly Glu Trp Val Pro Gly
                100                 105                 110
Gly Lys Pro Glu Pro Gln Ala Pro Ser Cys Val Tyr Ile His Pro Asp
            115                 120                 125
Ser Pro Asn Phe Gly Ala His Trp Met Lys Ala Pro Val Ser Phe Ser
        130                 135                 140
Lys Val Lys Leu Thr Asn Lys Leu Asn Gly Gly Gly Gln Ile Met Leu
145                 150                 155                 160
Asn Ser Leu His Lys Tyr Glu Pro Arg Ile His Ile Val Arg Val Gly
                165                 170                 175
Gly Pro Gln Arg Met Ile Thr Ser His Cys Phe Pro Glu Thr Gln Phe
            180                 185                 190
Ile Ala Val Thr Ala Arg Ser Asp His Lys Glu Met Met Glu Glu Pro
        195                 200                 205
Gly Asp Ser Gln Gln Pro Gly Tyr Ser Gln Trp Gly Trp Leu Leu Pro
    210                 215                 220
Gly Thr Ser Thr Xaa Cys Pro Pro Ala Asn Pro His Pro Gln Phe Gly
225                 230                 235                 240
```

-continued

```
Gly Ala Leu Ser Leu Pro Ser Thr His Ser Cys Asp Arg Tyr Pro Thr
                245                 250                 255

Leu Arg Ser His Arg Ser Ser Pro Tyr Pro Ser Pro Tyr Ala His Arg
            260                 265                 270

Asn Asn Ser Pro Thr Tyr Ser Asp Asn Ser Pro Ala Cys Leu Ser Met
        275                 280                 285

Leu Gln Ser His Asp Asn Trp Ser Ser Leu Gly Met Pro Ala His Pro
    290                 295                 300

Ser Met Leu Pro Val Ser His Asn Ala Ser Pro Pro Thr Ser Ser Ser
305                 310                 315                 320

Gln Tyr Pro Ser Leu Trp Ser Val Ser Asn Gly Ala Val Thr Pro Gly
                325                 330                 335

Ser Gln Ala Ala Ala Val Ser Asn Gly Leu Gly Ala Gln Phe Phe Arg
            340                 345                 350

Gly Ser Pro Ala His Tyr Thr Pro Leu Thr His Pro Val Ser Ala Pro
        355                 360                 365

Ser Ser Ser Gly Ser Pro Leu Tyr Glu Gly Ala Ala Ala Thr Asp
    370                 375                 380

Ile Val Asp Ser Gln Tyr Asp Ala Ala Ala Gln Gly Arg Leu Ile Ala
385                 390                 395                 400

Ser Trp Thr Pro Val Ser Pro Pro Ser Met
                405                 410

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Trp Leu Leu Pro Gly Thr Ser Thr Val
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Tyr Leu Ser Gly Ala Asp Leu Asn Leu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Ala Leu Trp Gly Gln Asp Val Thr Ser Val
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic
```

```
<400> SEQUENCE: 7

Lys Tyr His Pro Met Ser Glu Tyr Ala Leu
1               5                   10
```